United States Patent
Reaume et al.

(10) Patent No.: US 12,011,445 B2
(45) Date of Patent: Jun. 18, 2024

(54) PREVENTION OF PANCREATIC CELL DEGENERATION

(71) Applicant: Melior Pharmaceuticals I, Inc., Exton, PA (US)

(72) Inventors: Andrew G. Reaume, Exton, PA (US); Michael S. Saporito, Exton, PA (US); Alexander R. Ochman, Exton, PA (US)

(73) Assignee: Melior Pharmaceuticals I, Inc., Exton, PA (US)

( * ) Notice: Subject to any disclaimer, the term of this patent is extended or adjusted under 35 U.S.C. 154(b) by 0 days.

(21) Appl. No.: 16/546,595

(22) Filed: Aug. 21, 2019

(65) Prior Publication Data

US 2020/0215067 A1    Jul. 9, 2020

Related U.S. Application Data

(63) Continuation of application No. 13/700,191, filed as application No. PCT/US2011/038278 on May 27, 2011, now abandoned.

(60) Provisional application No. 61/349,231, filed on May 28, 2010.

(51) Int. Cl.
A61K 31/513    (2006.01)
A61P 3/10    (2006.01)

(52) U.S. Cl.
CPC .............. *A61K 31/513* (2013.01); *A61P 3/10* (2018.01)

(58) Field of Classification Search
CPC ................................ A61K 31/513; A61P 3/10
See application file for complete search history.

(56) References Cited

U.S. PATENT DOCUMENTS

| | | | |
|---|---|---|---|
| 3,174,901 | A | 3/1965 | Sterne |
| 3,922,345 | A | 11/1975 | Lipinski et al. |
| 4,080,454 | A | 3/1978 | Lipinski |
| 4,824,851 | A | 4/1989 | Takaya et al. |
| 5,476,855 | A | 12/1995 | el Kouni et al. |
| 5,698,155 | A | 12/1997 | Grosswald et al. |
| 5,721,114 | A | 2/1998 | Abrahamsen et al. |
| 5,721,241 | A | 2/1998 | el Kouni et al. |
| 6,004,925 | A | 12/1999 | Dasseux et al. |

(Continued)

FOREIGN PATENT DOCUMENTS

| | | |
|---|---|---|
| CN | 1395560 | 2/2003 |
| EP | 1541694 | 6/2005 |

(Continued)

OTHER PUBLICATIONS

Cnop et al., "Mechanisms of pancreatic beta cell death in type 1 and type 2 diabetes", Diabetes, 2005, vol. 54 supplement 2, pp. s97-s107. (Year: 2005).*

(Continued)

*Primary Examiner* — Craig D Ricci
*Assistant Examiner* — Janet L Coppins
(74) *Attorney, Agent, or Firm* — Armstrong Teasdale LLP

(57) ABSTRACT

The present invention relates to compounds and pharmaceutically acceptable salts thereof and formulations comprising the compounds or a pharmaceutically acceptable salts thereof that are useful in methods of preventing pancreatic beta cell degeneration or methods of treating a disorder associated with pancreatic beta cell degeneration, such as type I diabetes.

13 Claims, 2 Drawing Sheets

(56) References Cited

U.S. PATENT DOCUMENTS

| | | | |
|---|---|---|---|
| 6,037,323 | A | 3/2000 | Dasseux et al. |
| 6,410,255 | B1 | 6/2002 | Pollok et al. |
| 7,429,564 | B2 | 9/2008 | Arbit et al. |
| 7,776,870 | B2* | 8/2010 | Reaume .................. A61P 3/10 514/269 |
| 8,343,985 | B2 | 1/2013 | Reaume et al. |
| 8,835,448 | B2 | 9/2014 | Reaume et al. |
| 9,216,959 | B2 | 12/2015 | Reaume et al. |
| 10,251,883 | B2 | 4/2019 | Reaume et al. |
| 10,786,503 | B2 | 9/2020 | Reaume et al. |
| 11,033,548 | B2 | 6/2021 | Reaume et al. |
| 11,534,442 | B2 | 12/2022 | Reaume et al. |
| 2002/0151497 | A1 | 10/2002 | Ben-Sasson |
| 2005/0009817 | A1 | 1/2005 | Savoy et al. |
| 2005/0208054 | A1 | 9/2005 | Czech et al. |
| 2006/0024365 | A1 | 2/2006 | Vaya et al. |
| 2006/0035302 | A1 | 2/2006 | Lee |
| 2006/0252777 | A1 | 11/2006 | Kim et al. |
| 2007/0025953 | A1 | 2/2007 | Jones |
| 2007/0049609 | A1 | 3/2007 | Broka et al. |
| 2007/0093516 | A1* | 4/2007 | Reaume .................. A61P 15/10 514/269 |
| 2007/0185070 | A1 | 8/2007 | Pershadsingh |
| 2010/0004273 | A1 | 1/2010 | Reaume et al. |
| 2010/0278804 | A1 | 11/2010 | Reaume et al. |
| 2012/0046244 | A1 | 2/2012 | Rogers et al. |

FOREIGN PATENT DOCUMENTS

| | | |
|---|---|---|
| GB | 1377308 | 12/1974 |
| JP | 2007037546 | 2/2007 |
| WO | 199401414 | 1/1994 |
| WO | 200151463 | 7/2001 |
| WO | 2002068394 | 9/2002 |
| WO | 2002095058 | 11/2002 |
| WO | 2007024863 | 3/2007 |
| WO | 2009015133 | 1/2009 |
| WO | 2011150300 | 12/2011 |
| WO | 2015127474 | 8/2015 |

OTHER PUBLICATIONS

Hong et al., Biomol Ther 21(4), 284-289 (2013) (Year: 2013).*

Chang-Chen et al., Rev Endocr Metab Disord. 2008; 9(4): 329-343. (Year: 2008).*

Advisory Action dated Apr. 13, 2012 received in co-pending U.S. Appl. No. 12/837,067.

Blasioli et al., "Lyn/CD22/SHP-1 and their importance in autoimmunity", Curr Dir Autoimmun, 2002, 5, pp. 151-160.

Bozulic et al., "The influence of Lyn mkinase on Na, K-ATPase in porcine lens epithelium", Am J Physiol Cell Physiol, 2003, 286(1), pp. C90-C96.

Briggs et al., "Affinity of Src Family Kinase SH3 Domains for HIV Nef in vitro Does not Predict Kinase Activation by Nef in vivo", Biochemistry, 2000; 39, pp. 489-495.

Buchwald et al., "Long-term, continuous intravenous heparin administration by an implantable infusion pump in ambulatory patients with recurrent venous thrombosis", Surgery, 1987; 88(4), pp. 507-516.

Cnop et al., "Mechanisms of pancreatic beta cell death in type 1 and type 2 diabetes", Diabetes, 2005, v54 supplement 2, pp. s97-s107.

DeFronzo et al., "Mechanism of metformin action in obese and lean noninsulin-dependent diabetic subjects", J Clin Endocrinol Metab, 1991, 73(6), pp. 1294-1301.

DeWitt et al., "Outpatient Insulin Therapy in Type 1 and Type 2 Diabetes Mellitus", JAMA, 2003, v289(17), pp. 2254-2264 and pp. e1-e7.

During et al., "Controlled Release of Dopamine from a Polymeric Brain Implant: in vivo Characterization", Annals of Neurology, 1989, 25(4), pp. 351-356.

Final Office Action dated Apr. 17, 2017 in related U.S. Appl. No. 13/700,191.

Final Office Action dated Mar. 12, 2008 received in copending U.S. Appl. No. 11/507,652.

Final Office Action dated Sep. 18, 2019 in related U.S. Appl. No. 15/948,406.

Goodson, "Medical Applications Controlled Release", J Neurosurg, 1984, 2, pp. 115-138.

Howard et al., "Intracerebral drug delivery in rats with lesion-induced memory deficits", J Neurosurg, 1989, 71, pp. 105-112.

Ishikawa et al., "Requirements of src family kinase activity associated with CD45 for myeioma cell proliferation by interleukin-6", Blood, 2002, 99, pp. 2172-2178.

Johnson et al., "Phosphorylated immunoreceptor signaling motifs (ITAMs) exhibit unique abilities to bind and activate Lyn and Syk tyrosine kinases," J Immunol, 1995, 155(10), pp. 4596-4603.

Kidshealth, retrieved from http://kidshealth.org/parent!medical/endocrine/prevention.html on Sep. 8, 2015, 2 pages.

Langer and Wise, "Medical Applications of Controlled Release", CRC Pres, 1984, Boca Raton, FL.

Langer et al., "Chemical and Physical Structure of Polymers as Carriers for Controlled Release of Bioactive Agents: A Review", JMS-Rev Macromol Chem Phys, 1983, 23(1), pp. 61-126.

Langer, "New methods of drug delivery", Science, 1990, 249(4976), pp. 1527-1533.

Levy et al., "Inhibition of calcification of bioprosthetic heart valves by local controlled-release diphosphonate", Science, 1985, 228(4696), pp. 190-192.

Lipinski et al., "Bronchodilator and antiulcer phenoxypyrimidinones," J Med Chem, 1980, 23(9), pp. 1026-1031.

Lopez-Berestein, "Treatment of Systemic Fungal Infections with Liposomal-Amphotericin B", ibid., 1989, pp. 317-327.

Ma et al., "Activation of the cold-sensing TRPM8 channel triggers UCP1-dependent thermogenesis and prevents obesity", Journal of Molecular Biology, 2012, 4, pp. 88-96.

Masuda et al., "Peptic Ulcer in Diabetes Millitus", Gastroenterologia Japonica, 1976, 11(1), pp. 1-4.

Mayerson et al., "The effects of rosiglitazone on linsulin sensitivity, lipolysis, and hepatic and skeletal muscle triglyceride content in patients with type 2 diabetes", Diabetes, 2002, 51(3), pp. 797-802.

Mayo Clinic, definition (retrieved from http://www.mayoclinic.org/diseases-conditions/type-1-diabetes/basics/definition/con20019573 on Feb. 27, 2017, 3 pages).

MedlinePlus (retrieved from https://www.nlm.nih.gov/medlineplus/ency/article/000305.htm on Sep. 8, 2015, 10 pages).

Meyer et al., "The benefits of metformin therapy during continuous subcutaneous insulin infusion treatment of type 1 diabetic patients", Diabetes Care, 2002, v25(12), pp. 2153-2158.

Muller et al., "Interaction of phosphatidylinositolglycan(-peptides) with plasma membrane lipid rafts triggers insulin-mimetic signaling in rat adipocytes", Arch of Biochem Biophys, 2002, 408, pp. 7-16.

Non-final Office Action dated Apr. 12, 2018 in related U.S. Appl. No. 15/684,130.

Non-final Office Action dated Apr. 17, 2015 in related U.S. Appl. No. 14/182,380.

Non-Final Office Action dated Dec. 11, 2009 received in copending U.S. Appl. No. 11/507,652.

Non-Final Office Action dated Dec. 21, 2011 in co-pending U.S. Appl. No. 12/495,857.

Non-Final Office Action dated Feb. 4, 2019 in related U.S. Appl. No. 15/948,406.

Non-final Office Action dated Jul. 31, 2012 in co-pending U.S. Appl. No. 12/495,857.

Non-Final Office Action dated Jun. 27, 2012 received in co-pending U.S. Appl. No. 12/527,801.

Non-Final Office Action dated Mar. 20, 2009 received in copending U.S. Appl. No. 11/507,652.

Non-Final Office Action dated May 28, 2013 received in copending U.S. Appl. No. 13/690,548.

Non-Final Office Action dated Nov. 16, 2011 received in copending U.S. Appl. No. 12/837,067.

Non-Final Office Action dated Sep. 7, 2007 received in copending U.S. Appl. No. 11/507,652.

(56) References Cited

OTHER PUBLICATIONS

Non-Final Office Action dated Sep. 10, 2008 in related U.S. Appl. No. 11/507,652.
Notice of Allowance dated Apr. 9, 2010 received in copending U.S. Appl. No. 11/507,652.
Notice of Allowance dated Aug. 31, 2012 received in co-pending U.S. Appl. No. 12/837,067.
Notice of Allowance dated Aug. 17, 2015 in related U.S. Appl. No. 14/182,380.
Notice of Allowance dated Jan. 24, 2014 received in copending U.S. Appl. No. 13/690,548.
Notice of Allowance dated Jun. 6, 2013 received in copending U.S. Appl. No. 12/495,857.
Notice of Allowance dated May 26, 2017 in U.S. Appl. No. 14/941,473.
Notice of Allowance dated Nov. 28, 2018 related U.S. Appl. No. 15/684,130.
Ochman et al., "The Lyn Kinase Activator MLR-1023 is a Novel Insulin Receptor Potentiator that Elicits a Rapid-Onset and Durable Improvement in Glucose Homeostasis in Animal Models of Type 2 Diabetes", The Journal of Pharmacology and Experimental Therapeutics, 2012, 342(1), pp. 23-32.
Notice of Allowance dated May 21, 2020 in related U.S. Appl. No. 15/948,406.
Rossato et al., "Human white adipocytes express the cold receptor TRPM8 which activation induces UCP1 expression, mitochondrial activation and heat production", Molecular and Cellular Endocrinology, 2014, 383, pp. 137-146.
Office Action dated Dec. 30, 2016 in related U.S. Appl. No. 14/941,473.
Office Action dated Feb. 4, 2020 in related U.S. Appl. No. 16/286,976.
Pubchem, Substance Record for SID 313487653, http://pubchem.ncbi.nlm.nih.gov/substance/313487653.
Pubchem, Substance Record for SID 313508515, http://pubchem.ncbi.nlm.nih.gov/substance/313508515.
Raj et al., "Oral Insulin—A Perspective", Journal of Biomaterials Applications, 2003, 17, pp. 183-196.
Reaven, "Role of insulin resistance in human disease (syndrome X): an expanded definition", Annu Rev Med, 1993, 44, pp. 121-131.
Saporito et al., "MLR-1 023:a drug candidate for type II diabetes with a novel molecular target discovered using an in vivo repositioning approach", Chemical Information Bulletin, 2007, v59(2), p. 28.
Sefton, "Implantable Pumps", CRC Crit Ref Biomed Eng, 1987, 14(3), pp. 201-240.
Smolen and Ball, "Controlled Drug Bioavailability, Drug Product Design and Performance," Wiley, New York, 1984.
SRC Kinase, [on line], Jan. 12, 2006, URL, http://www.cellsignal.com/pdf/7775.pdf.
St. Charles et al., "Health economic comparison between continuous subcutaneous insulin infusion and multiple daily injections of insulin for the treatment of adult type 1 diabetes in Canada", Clinical Therapeutics Excerptra Medica, 2009, 31(3), pp. 657.
Summy et al., "AP23846, a novel and highly potent Src family kinase inhibitor, reduces vascular endothelial growth factor and interlieukin-8 expression in human solid tumor cell lines and abrogates downstream angiogenic processes", Mol CancerTher, 2005, 4(12), pp. 1900-1911.
Treat et al., "Liposomes in the Therapy of Infectious Disease and Cancer", Lopez-Berestein and Fidler (eds.), Liss, New York, 1989, pp. 353-365.
Wesch et al., "High throughput screening for protein kinase inhibitors", Comb Chem High Throughput Screen, 2005, 8(2), pp. 181-195.
Z-LYTE Kinase Assay Kits, 2008, Invitrogen website http://www.invitrogen.com.
Office Action dated Oct. 29, 2018 in related U.S. Appl. No. 14/364,792.
Office Action dated Oct. 16, 2017 in related U.S. Appl. No. 14/364,792.
Final Office Action dated Apr. 12, 2016 in related U.S. Appl. No. 14/364,792.
Non-final Office Action dated May 20, 2015 in related U.S. Appl. No. 14/364,792.
Non-final Office Action dated Oct. 7, 2015 in related U.S. Appl. No. 14/364,792.
Notice of Allowance dated Feb. 9, 2021 received in related U.S. Appl. No. 16/286,976.
Non-Final Office Action dated Feb. 19, 2021 in related U.S. Appl. No. 16/737,200.
Final Office Action dated Oct. 5, 2021 in related U.S. Appl. No. 16/737,200.
Final Office Action dated Jul. 21, 2022 in related U.S. Appl. No. 16/737,200.
Non-Final Office Action dated Feb. 9, 2022 in related U.S. Appl. No. 16/997,447.
Final Office Action dated Jun. 10, 2022 in related U.S. Appl. No. 16/997,447.
Notice of Allowance dated Aug. 24, 2022 in related U.S. Appl. No. 16/997,447.
Garcia et al., "Evaluation of markers of beige adipocytes in white adipose tissue of mouse", Nutrition and Metabolism, 2016, 13(14), pp. 1-14.
Non-Final Office Action dated Apr. 14, 2023 in related U.S. Appl. No. 16/737,200.
Non-Final Office Action dated Apr. 4, 2023 in related U.S. Appl. No. 17/314,543.
Advisory Action dated Nov. 20, 2023 in related U.S. Appl. No. 16/737,200.
Non-Final Office Action dated Dec. 12, 2023 in related U.S. Appl. No. 17/993,216.
Final Office Action dated Jan. 17, 2024 in related U.S. Appl. No. 17/314,543.

* cited by examiner

PREVENTION OF PANCREATIC CELL DEGENERATION

FIELD OF THE INVENTION

The present invention relates to compositions and formulations comprising therapeutically or prophylactically active compounds or pharmaceutically acceptable salts thereof, methods for preventing pancreatic beta cell degeneration, and methods for treating disorders associated with pancreatic beta cell degeneration. In particular, the compositions and formulations are useful for treating or preventing diseases and disorders including type I diabetes, comprising administering a composition comprising a therapeutically or prophylactically effective amount of a compound of the invention or a pharmaceutically acceptable salt thereof.

BACKGROUND OF THE INVENTION

Type I diabetes is characterized by a loss of insulin producing pancreatic β-cells. Compounds that prevent pancreatic β cell degeneration may be considered as potential therapeutics for the treatment of type I diabetes. db/db mice are an acceptable model of diabetes. These mice exhibit a progressive increase in blood glucose, decrease glucose utilization, a loss of circulating serum insulin and pancreatic β-cell degeneration. Results from a db/db study indicate that the compounds tested herein may be used for the prevention of pancreatic β-cell degeneration in type I diabetes.

SUMMARY OF THE INVENTION

The invention encompasses agents that may be useful in preventing pancreatic beta cell degeneration. In particular, the agents useful in preventing pancreatic beta cell degeneration include, but are not limited to, compositions and formulations comprising a compound of Formulas I-XI.

The invention also encompasses methods for treating or preventing a disease or disorder including, but not limited to, type I diabetes comprising administering to a subject, such as a mammal, in need thereof a therapeutically or prophylactically effective amount of a composition or formulation comprising a compound of the invention.

As described herein, the compositions that may be useful in the methods of the invention described herein encompass compounds of Formulas I-XI.

In one embodiment, the invention encompasses a composition comprising a compound of Formula (I):

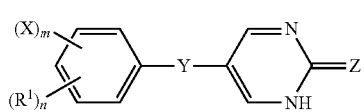

(I)

or a pharmaceutically acceptable salt and/or prodrug thereof, wherein $R^1$ is an alkyl group; X is a halogen; Y is O, S, or NH; Z is O or S; n is an integer from 0 to 5 and m is an integer from 0 to 5, wherein m+n is less than or equal to 5.

In another embodiment, the invention encompasses a composition comprising a compound of Formula (II):

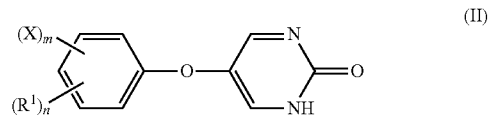

(II)

or a pharmaceutically acceptable salt and/or prodrug thereof, wherein $R^1$ is an alkyl group; X is a halogen; n is an integer from 0 to 5 and m is an integer from 0 to 5, wherein m+n is less than or equal to 5.

In yet another embodiment, the invention encompasses a composition comprising a compound of Formula (III):

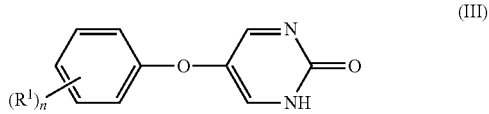

(III)

or a pharmaceutically acceptable salt and/or prodrug thereof, wherein $R^1$ is an alkyl group and n is an integer from 0 to 5.

In another embodiment, the invention encompasses a composition comprising a compound of Formula (IV):

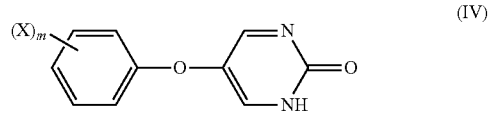

(IV)

or a pharmaceutically acceptable salt and/or prodrug thereof, wherein X is a halogen and m is an integer from 0 to 5.

In another embodiment, the invention encompasses a composition comprising a compound of Formula (V):

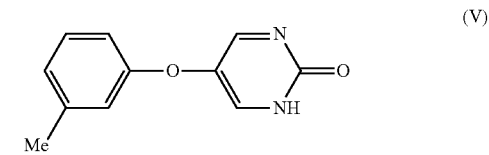

(V)

or a pharmaceutically acceptable salt and/or prodrug thereof.

In another embodiment, the invention encompasses a composition comprising a compound of Formula (VI):

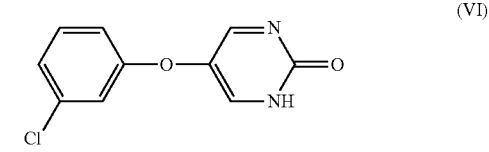 [SMILES: O=c1ncc(Oc2cccc(Cl)c2)c[nH]1]

(VI)

or a pharmaceutically acceptable salt and/or prodrug thereof.

In another embodiment, the invention encompasses a composition comprising a compound of Formula (VII):

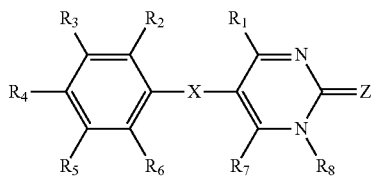

(VII)

wherein each of $R_1$, $R_2$, $R_3$, $R_4$, $R_5$, $R_6$, and $R_7$ are, independently, a hydrogen, alkoxy, alkyl, alkenyl, alkynyl, aryl, aryloxy, benzyl, cycloalkyl, halogen, heteroaryl, heterocycloalkyl, —CN, —OH, —NO$_2$, —CF$_3$, —CO$_2$H, —CO$_2$alkyl, or —NH$_2$; $R_8$ is an alkyl or hydrogen; X is O, S, NH, or N-akyl; and Z is O or S.

In another embodiment, the invention encompasses a composition comprising a compound of Formula (VIII):

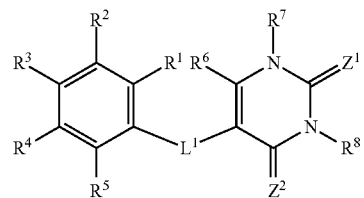

(VIII)

wherein:

$R^1$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, or S(O)$_2$NR$^{c1}$R$^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

$R^2$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, or S(O)$_2$NR$^{c1}$R$^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

$R^3$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, or S(O)$_2$NR$^{c1}$R$^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

$R^4$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, or S(O)$_2$NR$^{c1}$R$^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

$R^5$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, or S(O)$_2$NR$^{c1}$R$^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

or two adjacent groups of $R^1$, $R^2$, $R^3$, $R^4$, and $R^5$ can link to form a fused cycloalkyl or fused heterocycloalkyl group, each optionally substituted by 1, 2, or 3 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a2}$, SR$^{a2}$ C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

$R^6$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$^{d1}$; S(O)R$^{b1}$, S(O)NR$^{c1}$R$^{d1}$, S(O)$_2$R$^{b1}$, NR$^{c1}$S(O)$_2$R$^{b1}$, or S(O)$_2$ $NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^7$ is H, $C_{1-6}$alkyl, $C_{1-6}$haloalkyl, $C_{1-6}$hydroxyalkyl, $C(O)R^{b1}$, $C(O)NR^{c1}R^{d1}$; $C(O)OR^{a1}$, $S(O)R^{b1}$, $S(O)NR^{c1}R^{d1}$, $S(O)_2R^{b1}$, or $S(O)_2NR^{c1}R^{d1}$;

$R^8$ is H, $C_{1-6}$alkyl, $C_{1-6}$haloalkyl, $C_{1-6}$hydroxyalkyl, $C(O)R^{b1}$, $C(O)NR^{c1}R^{d1}$; $C(O)OR^{a1}$, $S(O)R^{b1}$, $S(O)NR^{c1}R^{d1}$, $S(O)_2R^{b1}$, or $S(O)_2NR^{c1}R^{d1}$;

$R^{a1}$, $R^{b1}$, $R^{c1}$, and $R^{d1}$ are each, independently, selected from H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

or $R^{c1}$ and $R^{d1}$ together with the N atom to which they are attached form a 4-, 5-, 6-, or 7-membered heterocycloalkyl group or heteroaryl group, each optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

$R^{a2}$, $R^{b2}$, $R^{c2}$, and $R^{d2}$ are each, independently, selected from H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

or $R^{c2}$ and $R^{d2}$ together with the N atom to which they are attached form a 4-, 5-, 6-, or 7-membered heterocycloalkyl group or heteroaryl group, each optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

$Z^1$ is O, S, or $NR^9$;

$R^9$ is H, OH, $C_{1-6}$alkoxy, $C_{1-6}$haloalkyl, $C_{1-6}$hydroxyalkyl, aryloxy, heteroaryloxy, CN, or $NO_2$;

$Z^2$ is O, S, or $NR^{10}$;

$R^{10}$ is H, OH, $C_{1-6}$alkoxy, $C_{1-6}$haloalkyl, $C_{1-6}$hydroxyalkyl, aryloxy, heteroaryloxy, CN, or $NO_2$;

$L^1$ is 0, S, or $NR^{11}$; and $R^{11}$ is H, $C_{1-6}$alkyl, $C_{1-6}$haloalkyl, $C_{1-6}$hydroxyalkyl, $C(O)R^{b1}$, $C(O)NR^{c1}R^{d1}$; $C(O)OR^{a1}$, $S(O)R^{b1}$, $S(O)NR^{c1}R^{d1}$, $S(O)_2R^{b1}$, or $S(O)_2NR^{c1}R^{d1}$; or a pharmaceutically acceptable salt thereof. In some embodiments, the compound is not 5-m-methylphenoxyuracil or a pharmaceutically acceptable salt thereof.

In another embodiment, the invention encompasses a composition comprising a compound of Formula (VIIIa):

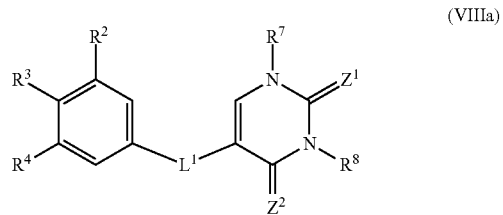

(VIIIa)

wherein:

$R^2$, $R^3$, and $R^4$ are each, independently, H, halo, $C_{1-6}$alkyl, $C_{1-6}$hydroxyalkyl, or $C_{1-6}$haloalkyl;

$R^7$ is H, $C_{1-6}$alkyl, $C(O)R^{b1}$, $C(O)NR^{c1}R^{d1}$, or $C(O)OR^{a1}$;

$R^8$ is H, $C_{1-6}$alkyl, $C(O)R^{b1}$, $C(O)NR^{c1}R^{d1}$, or $C(O)OR^{a1}$;

$R^{a1}$, $R^{b1}$, $R^{c1}$, and $R^{d1}$ are each, independently, selected from H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

or $R^{c1}$ and $R^{d1}$ together with the N atom to which they are attached form a 4-, 5-, 6-, or 7-membered heterocycloalkyl group or heteroaryl group, each optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

$Z^1$ is O or S;

$Z^2$ is O or S; and $L^1$ is O or S.

In another embodiment, the invention encompasses a composition comprising a compound of Formula (VIIIb):

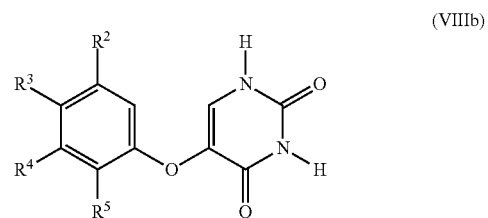

(VIIIb)

wherein:

$R^2$, $R^3$, $R^4$, and $R^5$ are each, independently, H, F, Cl, $CH_3$, $SCH_3$, $OCH_3$, $C(CH_3)_3$, $CH(CH_3)_2$, or $C_2H_5$.

In another embodiment, the invention encompasses a composition comprising a compound of (IX), Formula (X), or Formula (XI):

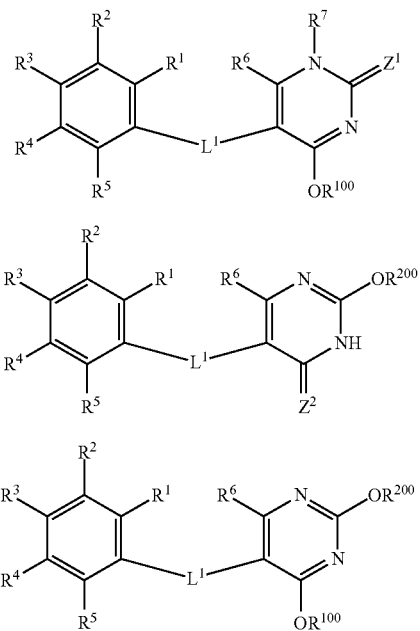

wherein:

R¹ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

R² is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$ $C(O)R^{b1}$, $C(O)NR^{c1}R^{d1}$, $C(O)OR^{a1}$ $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

R³ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

R⁴ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

R⁵ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

or two adjacent groups of R², R³, R⁴, and R⁵ can link to form a fused cycloalkyl or fused heterocycloalkyl group, each optionally substituted by 1, 2, or 3 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

R⁶ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c1}C(O)NR^{c2}R^{d2}$, $NR^{c2}(O)OR^{a2}$, $NR^{c2}S(O)NR^{c2}R^{d2}$, $S(O)R^{b2}$, $S(O)NR^{c2}R_{d2}$, $S(O)_2R^{b2}$, $NR^{c2}S(O)_2R^{b2}$, and $S(O)_2NR^{c2}R^{d2}$;

$R^7$ is H, $C_{1-6}$alkyl, $C_{1-6}$haloalkyl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, or $S(O)_2NR^{c1}R^{d1}$;

$R^{a1}$, $R^{b1}$, $R^{c1}$, and $R^{d1}$ are each, independently, selected from H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

or $R^{c1}$ and $R^{d1}$ together with the N atom to which they are attached form a 4-, 5-, 6-, or 7-membered heterocycloalkyl group or heteroaryl group, each optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

$R^{a2}$, $R^{b2}$, $R^{c2}$, and $R^{d2}$ are each, independently, selected from H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

or $R^{c2}$ and $R^{d2}$ together with the N atom to which they are attached form a 4-, 5-, 6-, or 7-membered heterocycloalkyl group or heteroaryl group, each optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

$Z^1$ is O, S, or $NR^9$;

$R^9$ is H, OH, $C_{1-6}$alkoxy, $C_{1-6}$haloalkyl, $C_{1-6}$hydroxyalkyl, aryloxy, heteroaryloxy, CN, or $NO_2$;

$Z^2$ is O, S, or $NR^{10}$;

$R^{10}$ is H, OH, $C_{1-6}$alkoxy, $C_{1-6}$haloalkyl, $C_{1-6}$hydroxyalkyl, aryloxy, heteroaryloxy, CN, or $NO_2$;

$L^1$ is O, S, or $NR^{11}$; and $R^{11}$ is H, $C_{1-6}$alkyl, $C_{1-6}$haloalkyl, $C_{1-6}$hydroxyalkyl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, or $S(O)_2NR^{c1}R^{d1}$;

$R^{100}$ is a hydroxyl protecting group, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, heterocycloalkyl, aryl, heteroaryl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, $S(O)_2NR^{c1}R^{d1}$, $S(O)_2OR^{e1}$, $P(O)OR^{f1}OR^{g1}$, or $Si(R^{h1})_3$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4 or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^{200}$ is a hydroxyl protecting group, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, heterocycloalkyl, aryl, heteroaryl, $C(O)R^{b1}{}_5$ $C(O)NR^{c1}R^{d1}$ $C(O)OR^{a1}$, $S(O)R^{b1}$, $S(O)NR^{c1}R^{d1}$, $S(O)_2R^{b1}$, $S(O)_2NR^{c1}R^{d1}$, $S(O)_2OR^{e1}$, $P(O)OR^{f1}OR^{g1}$, or $Si(R^{h1})_3$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4 or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

each $R^{e1}$ is, independently, H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, cycloalkylalkyl, heterocycloalkylalkyl, arylalkyl, or heteroarylalkyl;

each $R^{f1}$ is, independently, H, $C_{1-6}$alkyl, $C_{1-6}$haloalkyl, $C_{1-6}$hydroxyalkyl, $C_{2-6}$alkenyl, ($C_{1-6}$alkoxy)-$C_{1-6}$alkyl, $C_{2-6}$alkynyl, aryl, cycloalkyl, heteroaryl, heterocycloalkyl, arylalkyl, cycloalkylalkyl, heteroarylalkyl, or heterocycloalkylalkyl;

each $R^{g1}$ is, independently, H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, or heterocycloalkyl; and each $R^{h1}$ is, independently, H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, cycloalkylalkyl, heterocycloalkylalkyl, arylalkyl, or heteroarylalkyl;

or a pharmaceutically acceptable salt thereof.

The present invention may be understood more fully by reference to the figures, detailed description, and examples, which are intended to exemplify non-limiting embodiments of the invention.

DESCRIPTION OF EMBODIMENTS

Figure 1A:
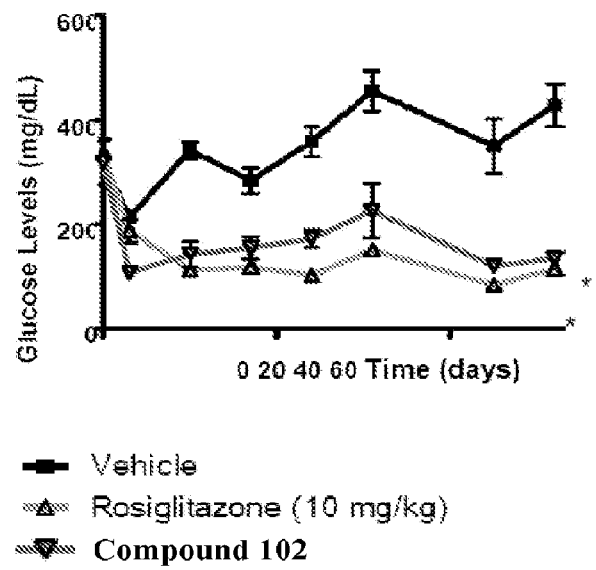
FIGS. 1A and B illustrate a decrease in blood glucose and prevention of the loss of serum insulin levels in db/db mice upon administration of Compound 102.

As used herein and unless otherwise indicated, the term "alkoxy group" means an —O-alkyl group, wherein alkyl is as defined herein. An alkoxy group can be unsubstituted or substituted with one or two suitable substituents. In some embodiments, the alkyl chain of an alkyloxy group is from 1 to 6 carbon atoms in length, referred to herein, for example, as "($C_1$-$C_6$)alkoxy."

As used herein and unless otherwise indicated, the term "alkyl" or "alkyl group" means a saturated, monovalent unbranched or branched hydrocarbon chain. Examples of alkyl groups include, but are not limited to, ($C_1$-$C_6$)alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl- 1-butyl, 2-ethyl-1-butyl, butyl, isobutyl, t-butyl, pentyl, isopentyl, neopentyl, and hexyl, and longer alkyl groups, such as heptyl, and octyl. An alkyl group can be unsubstituted or substituted with one or two suitable substituents.

As used herein and unless otherwise indicated, the term "alkenyl group" means a monovalent unbranched or branched hydrocarbon chain having one or more double bonds therein. The double bond of an alkenyl group can be unconjugated or conjugated to another unsaturated group. Suitable alkenyl groups include, but are not limited to ($C_2$-$C_6$)alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

As used herein and unless otherwise indicated, the term "alkynyl group" means monovalent unbranched or branched hydrocarbon chain having one or more triple bonds therein. The triple bond of an alkynyl group can be unconjugated or conjugated to another unsaturated group. Suitable alkynyl groups include, but are not limited to, ($C_2$-$C_6$)alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl. An alkynyl group can be unsubstituted or substituted with one or two suitable substituents.

As used herein and unless otherwise indicated, the term "aryl group" means a monocyclic or polycyclic-aromatic radical comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or two suitable substituents. In some embodiments, the aryl group is a monocyclic ring, wherein the ring comprises 6 carbon atoms, referred to herein as "($C_6$)aryl."

As used herein and unless otherwise indicated, the term "aryloxy group" means an —O-aryl group, wherein aryl is as defined herein. An aryloxy group can be unsubstituted or substituted with one or two suitable substituents. In some embodiments, the aryl ring of an aryloxy group is a monocyclic ring, wherein the ring comprises 6 carbon atoms, referred to herein as "($C_6$)aryloxy."

As used herein, the term "benzyl" means —$CH_2$-phenyl.

As used herein, the term "carbonyl" group is a divalent group of the formula —C(O)—.

As used herein and unless otherwise indicated, the term "compounds of the invention" means, collectively, the compounds of formulas I, II, III, IV, V, and VI and pharmaceutically acceptable salts thereof. The compounds of the invention are identified herein by their chemical structure and/or chemical name. Where a compound is referred to by both a chemical structure and a chemical name, and that chemical structure and chemical name conflict, the chemical structure is determinative of the compound's identity. The compounds of the invention may contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention, encompass all of the corresponding compound's enantiomers and stereoisomers, that is, both the stereomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically- or enantiomerically-pure intermediates, reagents, and catalysts by well known asymmetric synthetic methods.

As used herein and unless otherwise indicated, the term "cycloalkyl group" means a monocyclic or polycyclic saturated ring comprising carbon and hydrogen atoms and having no carbon-carbon multiple bonds. Examples of cycloalkyl groups include, but are not limited to, ($C_3$-$C_7$) cycloalkyl groups, such as cyclopropyl, cyclobutyl, cyclopentyl, cyclohexyl, and cycloheptyl, and saturated cyclic and bicyclic terpenes. A cycloalkyl group can be unsubstituted or substituted by one or two suitable substituents. In some embodiments, the cycloalkyl group is a monocyclic ring or bicyclic ring.

As used herein, the terms "diabetes" and "type I diabetes" are used interchangeably and refer to diabetes mellitus type 1, also known as IDDM or juvenile diabetes, which is a form of diabetes mellitus that results from autoimmune destruction of insulin-producing beta cells of the pancreas.

As used herein, the term "halogen" means fluorine, chlorine, bromine, or iodine. Correspondingly, the meaning of the terms "halo" and "Hal" encompass fluoro, chloro, bromo, and iodo.

As used herein and unless otherwise indicated, the term "heteroaryl group" means a monocyclic- or polycyclic aromatic ring comprising carbon atoms, hydrogen atoms, and one or more heteroatoms, suitably 1 to 3 heteroatoms, independently selected from nitrogen, oxygen, and sulfur. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidinyl, tetrazolyl, furyl, thienyl, isoxazolyl, thiazolyl, furyl, phienyl, isoxazolyl, and oxazolyl. A heteroaryl group can be unsubstituted or substituted with one or two suitable substituents. In some embodiments, a heteroaryl group is a monocyclic ring, wherein the ring comprises 2 to 5 carbon atoms and 1 to 3 heteroatoms, referred to herein as "($C_2$-$C_5$)heteroaryl."

As used herein and unless otherwise indicated, the term "heterocycloalkyl group" means a monocyclic or polycyclic ring comprising carbon and hydrogen atoms and at least one heteroatom, suitably, 1 to 3 heteroatoms selected from nitrogen, oxygen, and sulfur, and having no unsaturation. Examples of heterocycloalkyl groups include, but are not limited to, pyrrolidinyl, pyrrolidino, piperidinyl, piperidino, piperazinyl, piperazino, morpholinyl, morpholino, thiomorpholinyl, thiomorpholino, and pyranyl. A heterocycloalkyl group can be unsubstituted or substituted with one or two suitable substituents. In some embodiments, the heterocycloalkyl group is a monocyclic or bicyclic ring, or a monocyclic ring, wherein the ring comprises from 3 to 6 carbon atoms and form 1 to 3 heteroatoms, referred to herein as ($C_1$-$C_6$)heterocycloalkyl.

As used herein and unless otherwise indicated, the term "heterocyclic radical" or "heterocyclic ring" means a heterocycloalkyl group or a heteroaryl group.

As used herein and unless otherwise indicated, the term "hydrocarbyl group" means a monovalent group selected from ($C_1$-$C_8$)alkyl, ($C_2$-$C_8$)alkenyl, and ($C_2$-$C_8$)alkynyl, optionally substituted with one or two suitable substituents. In some embodiments, the hydrocarbon chain of a hydrocarbyl group is from 1 to 6 carbon atoms in length, referred to herein as "($C_1$-$C_6$)hydrocarbyl."

When administered to a mammal (e.g., to an animal for veterinary use or to a human for clinical use) the compounds of the invention may be administered in an isolated form. As used herein, "isolated" means that the compounds of the invention are separated from other components of either (a) a natural source, such as a plant or cell, such as bacterial culture, or (b) a synthetic organic chemical reaction mixture, such as, via conventional techniques, the compounds of the invention are purified. As used herein, "purified" means that when isolated, the isolate contains at least 90%, or at least 95%, or at least 98%, or at least 99% of a compound of the invention by weight of the isolate.

The phrase "pharmaceutically acceptable salt(s)," as used herein includes, but is not limited to, salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds, included in the present compositions, that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

The term "phenyl" means —$C_6H_5$. A phenyl group can be unsubstituted or substituted with one or two suitable substituents.

As used herein, a "suitable substituent" means a group that does not nullify the synthetic or pharmaceutical utility of the compounds of the invention or the intermediates useful for preparing them. Examples of suitable substituents include, but are not limited to: ($C_1$-$C_8$)alkyl, ($C_1$-$C_8$)alkenyl, ($C_1$-$C_8$)alkynyl, ($C_6$)aryl, ($C_3$-$C_5$)heteroaryl, ($C_3$-$C_7$)cycloalkyl, ($C_1$-$C_8$)alkoxy, ($C_6$)aryloxy, —CN, —OH, oxo, halo, —$NO_2$, —$CO_2H$, —$NH_2$, —NH(($C_1$-$C_8$)alkyl), —N(($C_1$-$C_8$)alkyl)$_2$, —NH(($C_6$)aryl), —N(($C_6$)aryl)$_2$, —CHO, —CO(($C_1$-$C_8$)alkyl), —CO(($C_6$)aryl), —$CO_2$(($C_1$-$C_8$)alkyl), and —$CO_2$(($C_6$)aryl). One of skill in art can readily choose a suitable substituent based on the stability and pharmacological and synthetic activity of the compound of the invention.

As used herein and unless otherwise indicated, the phrase "therapeutically effective amount" of a composition of the invention is measured by the therapeutic effectiveness of a compound of the invention, wherein at least one adverse effect of a disorder is ameliorated or alleviated. In one embodiment, the phrase "therapeutically effective amount" of a composition of the invention is measured by the therapeutic effectiveness of a compound of the invention to treat or prevent type I diabetes or to prevent or slow down the progression of pancreatic beta cell degeneration.

As used herein and unless otherwise indicated, the term "prevention" or "prevent", particularly in the context of pancreatic beta cell degeneration and/or type I diabetes, means a slowing down or reduction in pancreatic beta cell degeneration and/or type I diabetes. It need not mean the complete elimination of pancreatic beta cell degeneration and/or type I diabetes.

As set forth herein, the invention encompasses methods for preventing pancreatic beta cell degeneration, and methods for treating disorders associated with pancreatic beta cell degeneration such as type I diabetes, which comprises administering to a mammal in need of such treatment or prevention a therapeutically or prophylactically effective amount of a composition comprising a compound of Formula I-XI, or a pharmaceutically acceptable salt or prodrug thereof, and a pharmaceutically acceptable vehicle.

In some embodiments, the invention encompasses methods for preventing pancreatic beta cell degeneration, and methods for treating disorders associated with pancreatic beta cell degeneration such as type I diabetes, by administering a composition or formulation comprising a compound of Formula (VII):

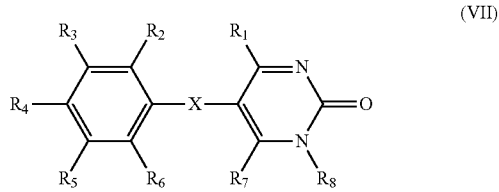

(VII)

wherein each of $R_1$, $R_2$, $R_3$, $R_4$, $R_5$, $R_6$, and $R_7$ are, independently, a hydrogen, alkoxy, alkyl, alkenyl, alkynyl, aryl, aryloxy, benzyl, cycloalkyl, halogen, heteroaryl, heterocycloalkyl, —CN, —OH, —$NO_2$, —$CF_3$, —$CO_2H$, —$CO_2$alkyl, or —$NH_2$;

$R_8$ is an alkyl or hydrogen;

X is O, S, NH, or N-akyl; and

Z is O or S.

In some embodiments, $R_8$ is alkyl, such as methyl. In some embodiments, $R_8$ is a hydrogen.

In some embodiments, X is oxygen. In some embodiments, Z is oxygen.

In some embodiments, at least one of $R_2$-$R_6$ is alkyl, such as methyl. In some embodiments, at least one of $R_2$-$R_6$ is halogen, such as chloro. In some embodiments, at least one of $R_2$-$R_6$ is CN. In some embodiments, at least one of $R_2$-$R_6$ is OH. In some embodiments, at least one of $R_2$-$R_6$ is $NO_2$. In some embodiments, at least one of $R_2$-$R_6$ is $CF_3$. In some embodiments, at least one of $R_2$-$R_6$ is $CO_2H$. In some embodiments, at least one of $R_2$-$R_6$ is $NH_2$. In some embodiment, at least one of $R_2$-$R_6$ is alkoxy.

In some embodiments, $R_2$ is alkyl, such as methyl and each of $R_1$, and $R_3$-$R_8$ is hydrogen and X and Z are O. In some embodiments, $R_2$ is a halogen, such as chloro, and each of $R_1$, and $R_3$-$R_8$ is hydrogen and X and Z are O.

In some embodiment, $R_3$ is alkyl, such as methyl and each of $R_1$, $R_2$ and $R_4$-$R_8$ is hydrogen and X and Z are O. In some embodiments, $R_3$ is a halogen, such as chloro, and each of $R_1$, $R_2$, and $R_4$-$R_8$ is hydrogen and X and Z are O.

In some embodiments, $R_4$ is alkyl, such as methyl and each of $R_1$- $R_3$ and $R_5$-$R_8$ is hydrogen and X and Z are O.

In some embodiments, $R_4$ is a halogen, such as chloro, and each of $R_1$-$R_3$, and $R_5$-$R_8$ is hydrogen and X and Z are O.

In some embodiments, $R_5$ is $CF_3$, and each of $R_1$-$R_4$ and $R_6$-$R_8$ is hydrogen and X and Z are O. In some embodiments, $R_5$ $NH_2$, and each of $R_1$-$R_4$ and $R_6$-$R_8$ is hydrogen and X and Z are O.

In some embodiments, $R_6$ is $CF_3$, and each of $R_1$- $R_5$ and $R_7$-$R_8$ is hydrogen and X and Z are O. In some embodiments, $R_6$ is $NH_2$ and each of $R_1$- $R_5$ and $R_7$-$R_8$ is hydrogen and X and Z are O.

In one embodiment, the invention encompasses a composition comprising a compound of Formula (I):

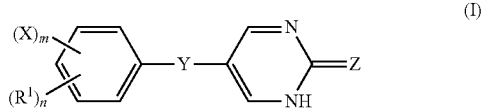

or a pharmaceutically acceptable salt and/or prodrug thereof, wherein $R^1$ is an alkyl group; X is a halogen; Y is O, S, or NH; Z is O or S; n is an integer from 0 to 5 and m is an integer from 0 to 5, wherein m +n is less than or equal to 5.

In some embodiments, the alkyl group is methyl and n is 1. In some embodiments, the halogen is chlorine and m is 1. In some embodiments, Y is O. In some embodiments, Z is O.

In some embodiments, $R_1$ is methyl, Y is O, Z is O, n is 1, and m is 0, where $R_1$ is in the meta position.

In some embodiments, X is chlorine, Y is O, Z is O, n is 0, and m is 1, where X is in the meta position. In some embodiments, the mammal is a human. In some embodiments, the effective amount is from about 0.1 mg to about 100 mg/kg, where the administration is oral.

In another embodiment, the invention encompasses a composition comprising a compound of Formula (II):

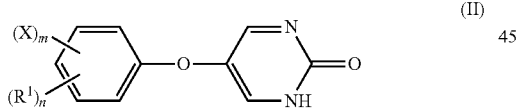

or a pharmaceutically acceptable salt and/or prodrug thereof, wherein $R^1$ is an alkyl group; X is a halogen; n is an integer from 0 to 5 and m is an integer from 0 to 5, wherein m +n is less than or equal to 5.

In yet another embodiment, the invention encompasses a composition comprising a compound of Formula (III):

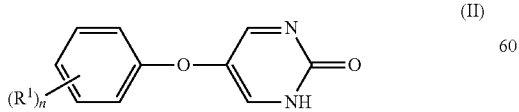

or a pharmaceutically acceptable salt and/or prodrug thereof, wherein $R^1$ is an alkyl group and n is an integer from 0 to 5.

In another embodiment, the invention encompasses a composition comprising a compound of Formula (IV):

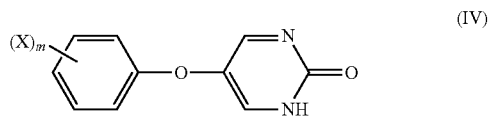

or a pharmaceutically acceptable salt and/or prodrug thereof, wherein X is a halogen and m is an integer from 0 to 5.

In another embodiment, the invention encompasses a composition comprising a compound of Formula (V):

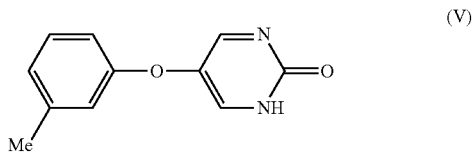 [SMILES: Cc1cccc(Oc2cnc(=O)[nH]c2)c1]

or a pharmaceutically acceptable salt and/or prodrug thereof.

In another embodiment, the invention encompasses a composition comprising a compound of Formula (VI):

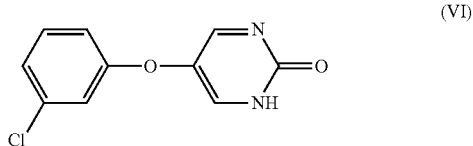 [SMILES: O=c1ncc(Oc2cccc(Cl)c2)c[nH]1]

or a pharmaceutically acceptable salt and/or prodrug thereof.

Illustrative examples of compounds that are encompassed by Formulas I-VII and that may be useful in the methods of the invention include, but are not limited to:

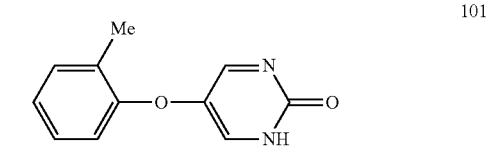
101

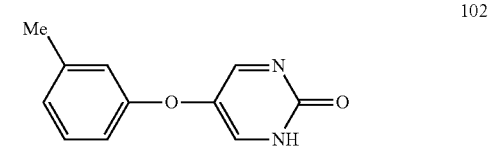
102

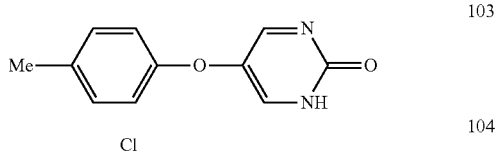
103

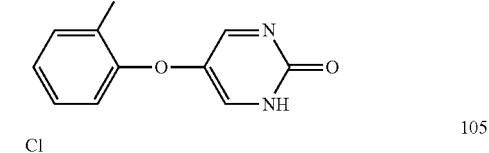
104

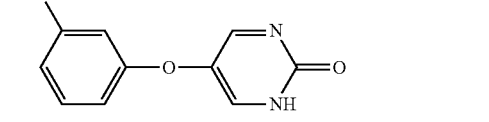
105

-continued

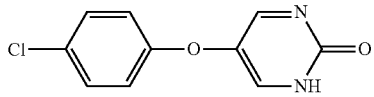
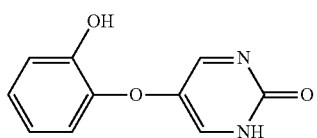
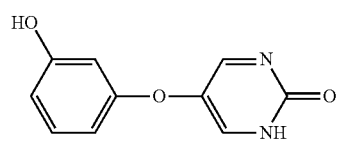
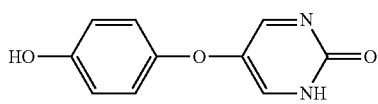
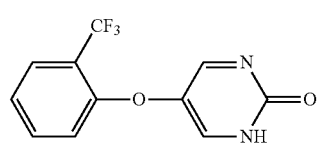
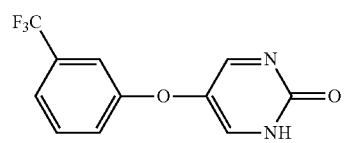
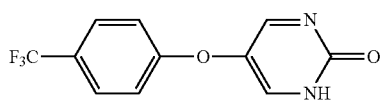
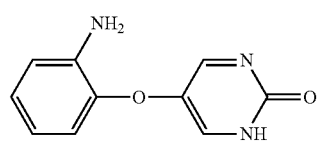
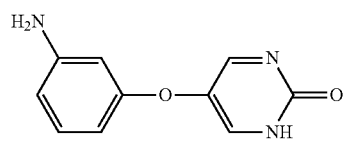
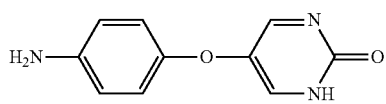

In another embodiment, the invention encompasses a composition comprising a compound of Formula (VIII):

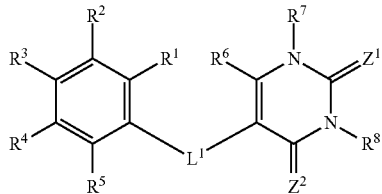

wherein:

$R^1$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{1-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^2$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^3$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^4$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$ $S(O)_2R^{b1}$, $S(O)_2R^{b1}$, or $S(O)_2NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^5$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)_2NR^{c1}R^{d1}$, $S(O)R^{b1}$, $S(O)NR^{c1}R^{d1}$, $S(O)_2R^{b1}$, $S(O)_2R^{b1}$, or $S(O)_2NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{d2}$, and $S(O)_2NR^{c2}R^{d2}$;

or two adjacent groups of $R^1$, $R^2$, $R^3$, $R^4$, and $R^5$ can link to form a fused cycloalkyl or fused heterocycloalkyl group, each optionally substituted by 1, 2, or 3 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{d2}$, $NR^{c2}S(O)_2R^{d2}$, and $S(O)_2NR^{c2}R^{d2}$;

$R^6$ is H, halo, $C_{1-6}$alkyl, $C_{2-6}$alkenyl, $C_{2-6}$alkynyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^7$ is H, $C_{1-6}$alkyl, $C_{1-6}$haloalkyl, $C_{1-6}$hydroxyalkyl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, or $S(O)_2NR^{c1}R^{d1}$;

$R^8$ is H, $C_{1-6}$alkyl, $C_{1-6}$haloalkyl, $C_{1-6}$hydroxyalkyl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, or $S(O)_2NR^{c1}R^{d1}$;

$R^{a1}$, $R^{b1}$, $R^{c1}$, and $R^{d1}$ are each, independently, selected from H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

or $R^{c1}$ and $R^{d1}$ together with the N atom to which they are attached form a 4-, 5-, 6-, or 7-membered heterocycloalkyl group or heteroaryl group, each optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

$R^{a2}$, $R^{b2}$, $R^{c2}$, and $R^{d2}$ are each, independently, selected from H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

or $R^{c2}$ and $R^{d2}$ together with the N atom to which they are attached form a 4-, 5-, 6-, or 7-membered heterocycloalkyl group or heteroaryl group, each optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

$Z^1$ is O, S, or $NR^9$;

$R^9$ is H, OH, $C_{1-6}$alkoxy, $C_{1-6}$haloalkyl, $C_{1-6}$hydroxyalkyl, aryloxy, heteroaryloxy, CN, or $NO_2$;

$Z^2$ is O, S, or $NR^{10}$;

$R^{10}$ is H, OH, $C_{1-6}$alkoxy, $C_{1-6}$haloalkyl, $C_{1-6}$hydroxyalkyl, aryloxy, heteroaryloxy, CN, or $NO_2$;

$L^1$ is O, S, or $NR^{11}$; and $R^{11}$ is H, $C_{1-6}$alkyl, $C_{1-6}$haloalkyl, $C_{1-6}$hydroxyalkyl, $C(O)R^{b1}$, $C(O)NR^{c1}R^{d1}$; $C(O)OR^{a1}$, $S(O)R^{b1}$, $S(O)NR^{c1}R^{d1}$, $S(O)_2R^{b1}$, or $S(O)_2NR^{c1}R^{d1}$;

or a pharmaceutically acceptable salt thereof.

In some embodiments, the compound is not 5-m-methylphenoxyuracil or a pharmaceutically acceptable salt thereof.

In some embodiments, $R^1$ and $R^5$ are each, independently, H, halo, $C_{1-6}$alkyl, $C_{1-6}$hydroxyalkyl, or $C_{1-6}$haloalkyl. In some embodiments, $R^1$ and $R^5$ are each, independently, H, halo, $C_{1-3}$alkyl, $C_{1-3}$hydroxyalkyl, or $C_{1-3}$haloalkyl. In some embodiments, $R^1$ and $R^5$ are each, independently, H or $C_{1-3}$alkyl. In some embodiments, $R^1$ and $R^5$ are both H.

In some embodiments, $R^2$, $R^3$, and $R^4$ are each, independently, H, halo, $C_{1-6}$alkyl, $C_{1-6}$hydroxyalkyl, or $C_{1-6}$haloalkyl. In some embodiments, $R^2$, $R^3$, and $R^4$ are each, independently, H, $C_{1-6}$alkyl, $C_{1-6}$hydroxyalkyl, or $C_{1-6}$haloalkyl. In some embodiments, $R^2$, $R^3$, and $R^4$ are each, independently, H or $C_{1-6}$alkyl. In some embodiments, $R^2$, $R^3$, and $R^4$ are each, independently, H or $C_{1-3}$alkyl.

In some embodiments, $R^6$ is H, halo, $C_{1-6}$alkyl, $C_{1-6}$hydroxyalkyl, or $C_{1-6}$haloalkyl. In some embodiments, $R^6$ is H or $C_{1-3}$alkyl. In some embodiments, $R^6$ is H.

In some embodiments, $R^7$ is H, $C_{1-6}$alkyl, $C(O)R^{b1}$, $C(O)NR^{c2}R^{a1}$, or $C(O)OR^{a1}$. In some embodiments, $R^7$ is H.

In some embodiments, $R^8$ is H, $C_{1-6}$alkyl, $C(O)R^{b1}$, $C(O)NR^{c1}R^{d1}$, or $C(O)OR^{a1}$. In some embodiments, $R^8$ is H.

In some embodiments, $Z^1$ is O or S. In some embodiments, $Z^1$ is O. In some embodiments, $Z^1$ is NH, N(OH), N—O—$C_{1-6}$alkyl, N—O-phenyl, CN, or $NO_2$.

In some embodiments, $Z^2$ is O. In some embodiments, $Z^2$ is S. In some embodiments, $Z^2$ is NH, N(OH), N—O—$C_{1-6}$alkyl, N—O-phenyl, CN, or $NO_2$.

In some embodiments, $L^1$ is O. In some embodiments, $L^1$ is S. In some embodiments, $L^1$ is NH or N($C_{1-6}$alkyl).

In another embodiment, the invention encompasses a composition comprising a compound of Formula (VIIIa):

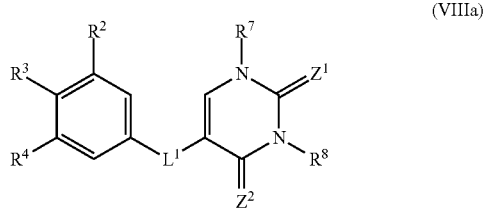

(VIIIa)

wherein:

$R^2$, $R^3$, and $R^4$ are each, independently, H, halo, $C_{1-6}$alkyl, $C_{1-6}$hydroxyalkyl, or $C_{1-6}$haloalkyl;

$R^7$ is H, $C_{1-6}$alkyl, $C(O)R^{b1}$, $C(O)NR^{c1}R^{d1}$, or $C(O)OR^{a1}$;

$R^8$ is H, $C_{1-6}$alkyl, $C(O)R^{b1}$, $C(O)NR^{c1}R^{d1}$, or $C(O)OR^{a1}$;

$R^{a1}$, $R^{b1}$, $R^{c1}$, and $R^{d1}$ are each, independently, selected from H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

or $R^{c1}$ and $R^{d1}$ together with the N atom to which they are attached form a 4-, 5-, 6-, or 7-membered heterocycloalkyl group or heteroaryl group, each optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

$Z^1$ is O or S;

$Z^2$ is O or S; and $L^1$ is O or S.

In some embodiments, the compound is not 5-m-methylphenoxyuracil or a pharmaceutically acceptable salt thereof.

In some embodiments, $L^1$ is O. In some embodiments, $L^1$ is S.

In some embodiments, $Z^1$ is O.

In some embodiments, $Z^2$ is O.

In some embodiments, $R^2$, $R^3$, and $R^4$ are each, independently, H, halo, $C_{1-3}$alkyl, $C_{1-3}$hydroxyalkyl, or $C_{1-3}$haloalkyl.

In some embodiments, $R^3$ is H.

In some embodiments, $R^2$ and $R^4$ is halo, $C_{1-3}$alkyl, $C_{1-3}$hydroxyalkyl, or $C_{1-3}$haloalkyl, and the other is H. In some embodiments, $R^2$ and $R^4$ is $C_{1-3}$alkyl, $C_{1-3}$hydroxyalkyl, or $C_{1-3}$haloalkyl, and the other is H. In some embodiments, $R^2$ and $R^4$ is $C_{1-3}$alkyl, and the other is H.

In some embodiments, $R^7$ and $R^8$ are each, independently, H, $C_{1-6}$alkyl, $C(O)$—($C_{1-6}$alkyl), or $C(O)$—O—($C_{1-6}$alkyl).

In some embodiments, $R^7$ and $R^8$ are each, independently, H or $C_{1-3}$alkyl. In some embodiments, $R^7$ and $R^8$ are both H.

In another embodiment, the invention encompasses a composition comprising a compound of Formula (VIIIb):

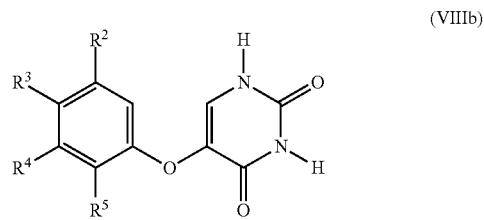

(VIIIb)

wherein:

$R^2$, $R^3$, $R^4$, and $R^5$ are each, independently, H, F, Cl, $CH_3$, $SCH_3$, $OCH_3$, $C(CH_3)_3$, $CH(CH_3)_2$, or $C_2H_5$.

In some embodiments, $R^2$, $R^3$, $R^4$, and $R^5$ are H. In some embodiments, $R^2$, $R^4$, and $R^5$ are H, and $R^3$ is $C_2H_5$. In some embodiments, $R^2$ and $R^5$ are H, $R^3$ is Cl, and $R^4$ is $C_2H_5$. In some embodiments, $R^2$, $R^4$, and $R^5$ are H, and $R^3$ is $OCH_3$. In some embodiments, $R^2$ and $R^5$ are H, $R^4$ is $CH_3$, and $R^3$ is $SCH_3$. In some embodiments, $R^3$, $R^4$, and $R^2$ are H, and $R^5$ is F. In some embodiments, $R^5$ is H, $R^4$ is $CH_3$, $R^3$ is Cl, and $R^2$ is $CH_3$. In some embodiments, $R^2$, $R^4$, and $R^5$ are H, and $R^3$ is $C(CH_3)_3$. In some embodiments, $R^2$, $R^3$, and $R^5$ are H, and $R^4$ is Cl. In some embodiments, $R^4$ and $R^2$ are H, $R^3$ is $CH_3$, and $R^5$ is $CH_3$. In some embodiments, $R^2$, $R^4$, $R^5$ are H, and $R^3$ is $SCH_3$. In some embodiments, $R^2$, $R^3$, and $R^5$ are H, and $R^4$ is $CH_3$. In some embodiments, $R^2$ and $R^5$ are H, $R^4$ is $CH_3$, and $R^3$ is Cl. In some embodiments, $R^2$, $R^4$, and $R^5$ are H, and $R^3$ is $CH(CH_3)_2$.

In another embodiment, the invention encompasses a composition comprising a compound of Formula (IX), Formula (X), or Formula (XI):

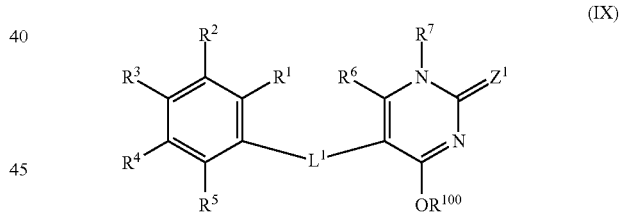

(IX)

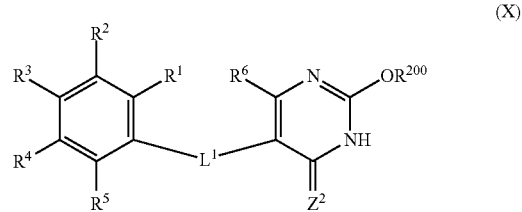

(X)

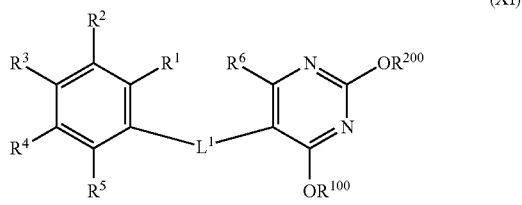

(XI)

wherein:

$R^1$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, or S(O)$_2$NR$^{c1}$R$^{d1}$, wherein each of said C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, and heteroaryl, is optionally substituted by 1, 2, 3, 4, or 5 substituents independently selected from halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

R$^2$ is H, halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c2}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, or S(O)$_2$NR$^{c1}$R$^{d1}$, wherein each of said C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, and heteroaryl, is optionally substituted by 1, 2, 3, 4, or 5 substituents independently selected from halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$^2$R$^{b2}$, NR$^{c2}$S(O)$_2$R$^{b2}$, and S(O)$_2$NR$^{c2}$R$^{d2}$;

R$^3$ is H, halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{a1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, or S(O)$_2$NR$^{c1}$R$^{d1}$, wherein each of said C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, and heteroaryl, is optionally substituted by 1, 2, 3, 4, or 5 substituents independently selected from halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

R$^4$ is H, halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, or S(O)$_2$NR$^{c1}$R$^{d1}$, wherein each of said C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, and heteroaryl, is optionally substituted by 1, 2, 3, 4, or 5 substituents independently selected from halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

R$^5$ is H, halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, or S(O)$_2$NR$^{c1}$R$^{d1}$, wherein each of said C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, and heteroaryl, is optionally substituted by 1, 2, 3, 4, or 5 substituents independently selected from halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

or two adjacent groups of R$^1$, R$^2$, R$^3$, R$^4$, and R$^5$ can link to form a fused cycloalkyl or fused heterocycloalkyl group, each optionally substituted by 1, 2, or 3 substituents independently selected from halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

R$^6$ is H, halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$_{d1}$; S(O)R$^{b1}$, S(O)NR$^{c1}$R$^{d1}$, S(O)$_2$R$^{b1}$, NR$^{c1}$S(O)$_2$R$^{b1}$, or S(O)$_2$NR$^{c1}$R$^{d1}$, wherein each of said C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, and heteroaryl, is optionally substituted by 1, 2, 3, 4, or 5 substituents independently selected from halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$D(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

R$^7$ is H, C$_{1-6}$alkyl, C$_{1-6}$haloalkyl, C(O)R$^{b1}$, C(O)NR$^{c1}$R$^{d1}$, C(O)OR$^{a1}$, S(O)R$^{b1}$, S(O)NR$^{c1}$R$^{d1}$, S(O)$_2$R$^{b1}$, or S(O)$_2$NR$^{c1}$R$^{d1}$;

R$^{a1}$, R$^{b1}$, R$^{c1}$, and R$^{d1}$ are each, independently, selected from H, C$_{1-6}$alkyl, C$_{1-6}$haloalkyl, C$_{1-6}$hydroxyalkyl, C$_{2-6}$alkenyl, C$_{2-6}$alkynyl, aryl, cycloalkyl, heteroaryl, heterocycloalkyl, arylalkyl, heteroarylalkyl, cycloalkylalkyl, and heterocycloalkylalkyl, wherein each of said C$_{1-6}$alkyl, C$_{1-6}$haloalkyl, C$_{1-6}$hydroxyalkyl, C$_{2-6}$alkenyl, C$_{2-6}$alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from OH, NO$_2$, CN, amino, halo, C$_{1-6}$alkyl, C$_{1-6}$alkoxy, C$_{1-6}$haloalkyl, C$_{1-6}$hydroxyalkyl, and C$_{1-6}$haloalkoxy;

or R$^{c1}$ and R$^{d1}$ together with the N atom to which they are attached form a 4-, 5-, 6-, or 7-membered heterocycloalkyl group or heteroaryl group, each optionally substituted with 1, 2, or 3 substituents independently selected from OH, NO$_2$, CN, amino, halo, C$_{1-6}$alkyl, C$_{1-6}$alkoxy, C$_{1-6}$haloalkyl, C$_{1-6}$hydroxyalkyl, and C$_{1-6}$haloalkoxy;

R$^{a2}$, R$^{b2}$, R$^{c2}$, and R$^{d2}$ are each, independently, selected from H, C$_{1-6}$alkyl, C$_{1-6}$hydroxyalkyl, C$_{2-6}$alkenyl, C$_{2-6}$alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

or $R^{c2}$ and $R^{d2}$ together with the N atom to which they are attached form a 4-, 5-, 6-, or 7-membered heterocycloalkyl group or heteroaryl group, each optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

$Z^1$ is O, S, or $NR^9$;

$R^9$ is H, OH, $C_{1-6}$alkoxy, $C_{1-6}$haloalkyl, $C_{1-6}$hydroxyalkyl, aryloxy, heteroaryloxy, CN, or $NO_2$;

$Z^2$ is O, S, or $NR^{10}$;

$R^{10}$ is H, OH, $C_{1-6}$alkoxy, $C_{1-6}$haloalkyl, $C_{1-6}$hydroxyalkyl, aryloxy, heteroaryloxy, CN, or $NO_2$;

$L^1$ is O, S, or $NR^{11}$; and $R^{11}$ is H, $C_{1-6}$alkyl, $C_{1-6}$haloalkyl, $C_{1-6}$hydroxyalkyl, $C(O)R^{b1}$, $C(O)NR^{c1}R^{d1}$, $C(O)OR^{a1}$, $S(O)R^{b1}$, $S(O)N^{c1}R^{d1}$, $S(O)_2R^{b1}$, or $S(O)_2N^{c1}R^{d1}$;

$R^{100}$ is a hydroxyl protecting group, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, heterocycloalkyl, aryl, heteroaryl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, $S(O)_2NR^{c1}R^{d1}$, $S(O)_2OR^{e1}$, $P(O)OR^{f1}OR^{g1}$, or $Si(R^{h1})_3$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4 or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^{200}$ is a hydroxyl protecting group, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, heterocycloalkyl, aryl, heteroaryl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, $S(O)_2NR^{c1}R^{d1}$, $S(O)_2OR^{c1}$, $P(O)OR^{f1}R^{g1}$, or $Si(R^{h1})_3$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4 or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

each $R^{e1}$ is, independently, H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, cycloalkylalkyl, heterocycloalkylalkyl, arylalkyl, or heteroarylalkyl;

each $R^{f1}$ is, independently, H, $C_{1-6}$alkyl, $C_{1-6}$haloalkyl, $C_{1-6}$hydroxyalkyl, $C_{2-6}$alkenyl, ($C_{1-6}$alkoxy)-$C_{1-6}$alkyl, $C_{2-6}$alkynyl, aryl, cycloalkyl, heteroaryl, heterocycloalkyl, arylalkyl, cycloalkylalkyl, heteroarylalkyl, or heterocycloalkylalkyl;

each $R^{g1}$ is, independently, H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, or heterocycloalkyl; and each $R^{h1}$ is, independently, H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, cycloalkylalkyl, heterocycloalkylalkyl, arylalkyl, or heteroarylalkyl;

or a pharmaceutically acceptable salt thereof.

In some embodiments, for a compound of Formula II, when $Z^1$ is O or S, $R^7$ is H, and $L^1$ is O, S, or $NR^{11}$, wherein $R^{11}$ is H or $C_{1-6}$alkyl, then $R^{100}$ is not $C_{1-6}$alkyl or aryl.

In some embodiments, $R^1$ and $R^5$ are each, independently, H, halo, $C_{1-6}$alkyl, $C_{1-6}$hydroxyalkyl, or $C_{1-6}$haloalkyl. In some embodiments, $R^1$ and $R^5$ are each, independently, H, halo, $C_{1-3}$alkyl, $C_{1-3}$hydroxyalkyl, or $C_{1-3}$haloalkyl. In some embodiments, $R^1$ and $R^5$ are each, independently, H or $C_{1-3}$alkyl. In some embodiments, $R^1$ and $R^5$ are both H.

In some embodiments, $R^2$, $R^3$, and $R^4$ are each, independently, H, halo, $C_{1-6}$alkyl, $C_{1-6}$hydroxyalkyl, or $C_{1-6}$haloalkyl. In some embodiments, $R^2$, $R^3$, and $R^4$ are each, independently, H, $C_{1-6}$alkyl, $C_{1-6}$hydroxyalkyl, or $C_{1-6}$haloalkyl. In some embodiments, $R^2$, $R^3$, and $R^4$ are each, independently, H or $C_{1-6}$alkyl. In some embodiments, $R^2$, $R^3$, and $R^4$ are each, independently, H or $C_{1-3}$alkyl.

In some embodiments, $R^6$ is H, halo, $C_{1-6}$alkyl, $C_{1-6}$hydroxyalkyl, or $C_{1-6}$haloalkyl. In some embodiments, $R^6$ is H or $C_{1-3}$alkyl. In some embodiments, $R^6$ is H.

In some embodiments, $R^7$ is H, $C_{1-6}$alkyl, $C(O)R^{b1}$, $C(O)NR^{c1}$ or $C(O)OR^{a1}$. In some embodiments, $R^7$ is H.

In some embodiments, $Z^1$ is O or S. In some embodiments, $Z^1$ is O. In some embodiments, $Z^1$ is NH, N(OH), N—O-$C_{1-6}$alkyl, N—O-phenyl, CN, or $NO_2$.

In some embodiments, $Z^2$ is O. In some embodiments, $Z^2$ is S. In some embodiments, $Z^2$ is NH, N(OH), N—O-$C_{1-6}$alkyl, N—O-phenyl, CN, or $NO_2$.

In some embodiments, $L^1$ is O. In some embodiments, $L^1$ is S. In some embodiments, $L^1$ is NH or N($C_{1-6}$alkyl).

In some embodiments, $R^{100}$ is a hydroxyl protecting group, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, heterocycloalkyl, aryl, or heteroaryl, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{1-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$.

In some embodiments, $R^{200}$ is a hydroxyl protecting group, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, heterocycloalkyl, aryl, or heteroaryl, wherein each of said $C_{1-6}$alkyl, $C_{2-6}$alkenyl, $C_{2-6}$alkynyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$.

An illustrative example of a compound that is encompassed by Formulas (VIII) and (VIIIa) includes, but is not limited to:

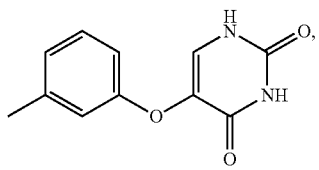

116 which is also known as 5-(m-tolyloxy)pyrimidine-2,4(1H,3H)-dione.

It will be understood that above compounds are illustrative only and not intended to limit the scope of the claims to only those compounds.

The compounds of the invention can be synthesized by organic chemistry techniques known to those of ordinary skill in the art, for example as described in U.S. Pat. Nos. 3,922,345 and 4,080,454, each of which is incorporated herein by reference in its entirety.

Preparation of the compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, $3^{rd}$ Ed., Wiley & Sons, Inc., New York (1999), which is incorporated herein by reference in its entirety. Suitable hydroxyl protecting groups include, but are not limited to, tert-butyldimethylsilyl (TBS), methoxymethyl ether (MOM), tetrahydropyranyl ether (THP), t-Butyl ether, allyl ether, benzyl ether, t-Butyldimethylsilyl ether (TBDMS), t-Butyldiphenylsilyl ether (TBDPS), acetic acid ester, and the like.

The invention encompasses compounds for preventing pancreatic beta cell degeneration, and for treating disorders associated with pancreatic beta cell degeneration such as type I diabetes.

In some embodiments, a composition of the invention comprising a compound of the invention and a pharmaceutically acceptable vehicle, is administered to a mammal, such as a human, with pancreatic beta cell degeneration and/or disorders associated with pancreatic beta cell degeneration, such as type I diabetes.

In one embodiment, "treatment" or "treating" refers to an amelioration of a disease or disorder, or at least one discernible symptom thereof, preferably associated with pancreatic beta cell degeneration. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

In some embodiments, the compositions of the invention are administered to a patient, such as a human, as a preventative measure against such diseases and disorders. As used herein, "prevention" or "preventing" refers to a reduction of the risk of acquiring a given disease or disorder. In some embodiments, the compositions of the present invention are administered as a preventative measure to a patient, such as a human having a genetic predisposition to type I diabetes.

As used herein, "treatment or prevention of diabetes" encompasses treatment or prevention of a complication associated with type I diabetes including, but not limited to, retinopathy (i.e., blindness); neuropathy (i.e., nerve damage) which leads to foot ulcers, gangrene, and amputations; kidney damage, which leads to dialysis; and cardiovascular disease.

The invention provides methods of treatment and prophylaxis by administration to a patient of a therapeutically effective amount of a composition comprising a compound of the invention. The patient is a mammal, including, but not limited to, an animal such a cow, horse, sheep, pig, chicken, turkey, quail, cat, dog, mouse, rat, rabbit, guinea pig, etc., and is more suitably a human.

The present compositions, which comprise one or more compounds of the invention, can be administered orally. The compounds of the invention may also be administered by any other convenient route, for example, by infusion or bolus injection, by absorption through epithelial or mucocutaneous linings (e.g., oral mucosa, rectal and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer a compound of the invention. In some embodiments, more than one compound of the invention is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The suitable mode of administration is left to the discretion of the practitioner, and will depend in-part upon the site of the medical condition. In most instances, administration will result in the release of the compounds of the invention into the bloodstream.

In some embodiments, it may be desirable to administer one or more compounds of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of an atherosclerotic plaque tissue.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

In another embodiment, the compounds of the invention can be delivered in a vesicle, in particular a liposome (see Langer, Science, 1990, 249, 1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In some embodiments, the compounds of the invention can be delivered in a controlled release system. In one embodiment, a pump may be used (see Langer, supra; Sefton, 1987, *CRC Crit. Ref Biomed. Eng.* 14:201; Buchwald et al., 1980, *Surgery* 88:507 Saudek et al., 1989, *N. Engl. J. Med.* 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). In some embodiments, a controlled-release system can be placed in proximity of the target of the compounds of the invention, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, 1990, *Science* 249:1527-1533) may be used.

The present compositions may contain a therapeutically effective amount of a compound of the invention, optionally more than one compound of the invention, optionally in purified form, together with a suitable amount of a pharmaceutically acceptable vehicle so as to provide the form for proper administration to the patient.

In some embodiments, the term "pharmaceutically acceptable" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compounds of the invention and pharmaceutically acceptable vehicles are suitably sterile. Water is a suitable vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in Remington's Pharmaceutical Sciences, A. R. Gennaro (Editor) Mack Publishing Co.

In some embodiments, the compounds of the invention are formulated in accordance with routine procedures as a pharmaceutical composition adapted for intravenous administration to human beings. Typically, compounds of the invention for intravenous administration are solutions in sterile isotonic aqueous buffer. Where necessary, the compositions may also include a solubilizing agent. Compositions for intravenous administration may optionally include a local anesthetic such as lidocaine to case pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound of the invention is to be administered by infusion, it can be dispensed, for example, with an infusion bottle containing sterile pharmaceutical grade water or saline. Where the compound of the invention is administered by injection, an ampoule of sterile water for injection or saline can be provided so that the ingredients may be mixed prior to administration.

The compositions of the invention can be administered orally. Compositions for oral delivery may be in the form of tablets, lozenges, aqueous or oily suspensions, granules, powders, emulsions, capsules, syrups, or elixirs, for example. Orally administered compositions may contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

The amount of a compound of the invention that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. However, suitable dosage ranges for oral administration are generally about 0.001 milligram to 200 milligrams of a compound of the invention per kilogram body weight. In some embodiments of the invention, the oral dose is 0.01 milligram to 70 milligrams per kilogram body weight, or 0.1 milligram to 50 milligrams per kilogram body weight, or 0.5 milligram to 20 milligrams per kilogram body weight, or 1 milligram to 10 milligrams per kilogram body weight. In some embodiments, the oral dose is 5 milligrams of a compound of the invention per kilogram body weight. The dosage amounts described herein refer to total amounts administered; that is, if more than one compound of the invention is administered, the dosages correspond to the total amount of the compounds of the invention administered. Oral compositions can contain 10% to 95% active ingredient by weight.

Suitable dosage ranges for intravenous (i.v.) administration are 0.01 milligram to 100 milligrams per kilogram body weight, 0.1 milligram to 35 milligrams per kilogram body weight, and 1 milligram to 10 milligrams per kilogram body weight. Suitable dosage ranges for intranasal administration are generally about 0.01 pg/kg body weight to 1 mg/kg body weight. Suppositories generally contain 0.01 milligram to 50 milligrams of a compound of the invention per kilogram body weight and comprise active ingredient in the range of 0.5% to 10% by weight. Recommended dosages for intradermal, intramuscular, intraperitoneal, subcutaneous, epidural, sublingual, intracerebral, intravaginal, transdermal administration or administration by inhalation are in the range of 0.001 milligram to 200 milligrams per kilogram of body weight. Suitable doses of the compounds of the invention for topical administration are in the range of 0.001 milligram to 1 milligram, depending on the area to which the compound is administered. Effective doses may be extrapolated from dose-response curves derived from in vitro or animal model test systems. Such animal models and systems are well known in the art.

The invention also provides pharmaceutical packs or kits comprising one or more containers filled with one or more compounds of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a some embodiments, the kit contains more than one compound of the invention. In some embodiments, the kit comprises a compound of the invention and another lipid-mediating compound, including but not limited to a statin, a thiazolidinedione, or a fibrate.

The compounds of the invention can be assayed in vitro and in vivo, for the desired therapeutic or prophylactic activity, prior to use in humans. For example, in vitro assays can be used to determine whether administration of a specific compound of the invention or a combination of compounds of the invention is suitable for lowering fatty acid synthesis. The compounds of the invention may also be demonstrated to be effective and safe using animal model systems.

Other methods will be known to the skilled artisan and are within the scope of the invention.

In some embodiments of the invention, the compounds of the invention can be used in combination therapy with at least one other therapeutic agent. The compound of the invention and the therapeutic agent can act additively or synergistically. In some embodiments, a composition comprising a compound of the invention is administered concurrently with the administration of another therapeutic agent, which can be part of the same composition as the compound of the invention or a different composition. In another embodiment, a composition comprising a compound of the invention is administered prior or subsequent to administration of another therapeutic agent. As many of the disorders for which the compounds of the invention are useful in treating are chronic disorders, in one embodiment combination therapy involves alternating between administering a composition comprising a compound of the invention and a composition comprising another therapeutic agent, e.g., to minimize the toxicity associated with a particular drug. The duration of administration of each drug or therapeutic agent can be, e.g., one month, three months, six months, or a year. In certain embodiments, when a composition of the invention is administered concurrently with another therapeutic agent that potentially produces adverse side effects including, but not limited to, toxicity, the therapeutic agent can advantageously be administered at a dose that falls below the threshold at which the adverse side is elicited.

The present compositions can be administered together with a statin. Statins for use in combination with the compounds of the invention include, but are not limited to, atorvastatin, pravastatin, fluvastatin, lovastatin, simvastatin, and cerivastatin.

The present compositions can also be administered together with a PPAR agonist, for example a thiazolidinedione or a fibrate. Thiazolidinediones for use in combination with the compounds of the invention include, but are not limited to, 5((4-(2-(methyl-2-pyridinylamino)ethoxy)phenyl)methyl)-2,4-thiazolidinedione, troglitazone, pioglitazone, ciglitazone, WAY-120,744, englitazone, AD 5075, darglitazone, and rosiglitazone. Fibrates for use in combination with the compounds of the invention include but are not limited to gemfibrozil, fenofibrate, clofibrate, or ciprofibrate. As mentioned previously, a therapeutically effective amount of a fibrate or thiazolidinedione often has toxic side effects. Accordingly, in some embodiments, when a composition of the invention is administered in combination with a PPAR agonist, the dosage of the PPAR agonist is below that which is accompanied by toxic side effects.

The present compositions can also be administered together with a bile-acid-binding resin. Bile-acid-binding resins for use in combination with the compounds of the invention include, but are not limited to, cholestyramine and colestipol hydrochloride.

The present compositions can also be administered together with niacin or nicotinic acid.

The present compositions can also be administered together with a RXR agonist. RXR agonists for use in combination with the compounds of the invention include, but are not limited to, LG 100268, LGD 1069, 9-cis retinoic acid, 2-(1-(3,5,5,8,8-pentamethyl-5,6,7,8-tetrahydro-2-naphthyl)-cyclopropyl)-pyridine-5-carboxylic acid, or 4-((3,5,5,8,8-pentamethyl-5,6,7,8-tetrahydro-2-naphthyl)2-carbonyl)-benzoic acid.

The present compositions can also be administered together with an anti-obesity drug. Anti-obesity drugs for use in combination with the compounds of the invention include, but are not limited to, β-adrenergic receptor agonists, such as β-3 receptor agonists, sibutramine, bupropion, fluoxetine, and phentermine.

The present compositions can also be administered together with a hormone. Hormones for use in combination with the compounds of the invention include, but are not limited to, thyroid hormone, estrogen and insulin. Suitable insulins include, but are not limited to, injectable insulin, transdermal insulin, inhaled insulin, or any combination thereof. As an alternative to insulin, an insulin derivative, secretagogue, sensitizer or mimetic may be used. Insulin secretagogues for use in combination with the compounds of the invention include, but are not limited to, forskolin, dibutryl cAMP or isobutylmethylxanthine (IBMX).

The present compositions can also be administered together with a tyrophostine or an analog thereof. Tyrophostines for use in combination with the compounds of the invention include, but are not limited to, tryophostine 51.

The present compositions can also be administered together with sulfonylurea-based drugs. Sulfonylurea-based drugs for use in combination with the compounds of the invention include, but are not limited to, glisoxepid, glyburide, acetohexamide, chlorpropamide, glibornuride, tolbutamide, tolazamide, glipizide, gliclazide, gliquidone, glyhexamide, phenbutamide, and tolcyclamide.

The present compositions can also be administered together with a biguanide. Biguanides for use in combination with the compounds of the invention include, but are not limited to, metformin, phenformin and buformin.

The present compositions can also be administered together with an a-glucosidase inhibitor. α-glucosidase inhibitors for use in combination with the compounds of the invention include, but are not limited to, acarbose and miglitol.

The present compositions can also be administered together with an apo A-I agonist. In one embodiment, the apo A-1 agonist is the Milano form of apo A-1 (apo A-1M). In some embodiments, the apo A-TM for administration in conjunction with the compounds of the invention is produced by the method of U.S. Pat. No. 5,721,114 to Abrahamsen. In some embodiments, the apo A-I agonist is a peptide agonist. In some embodiments, the apo A-I peptide agonist for administration in conjunction with the compounds of the invention is a peptide of U.S. Pat. No. 6,004,925 or 6,037,323.

The present compositions can also be administered together with apolipoprotein E (apo E). In some embodiments, the apoE for administration in conjunction with the compounds of the invention is produced by the method of U.S. Pat. No. 5,834,596.

In some embodiments, the present compositions can be administered together with an HDL-raising drug; an HDL enhancer; or a regulator of the apolipoprotein A-I, apolipoprotein A-IV and/or apolipoprotein genes.

The present compositions can be administered together with a known cardiovascular drug. Cardiovascular drugs for use in combination with the compounds of the invention to prevent or treat cardiovascular diseases include, but are not limited to, peripheral anti-adrenergic drugs, centrally acting antihypertensive drugs (e.g., methyldopa, methyldopa HCl), antihypertensive direct vasodilators (e.g., diazoxide, hydralazine HCl), drugs affecting renin-angiotensin system, peripheral vasodilators, phentolamine, antianginal drugs, cardiac glycosides, inodilators (e.g., amrinone, milrinone, enoximone, fenoximone, imazodan, sulmazole), antidysrhythmic drugs, calcium entry blockers, ranitine, bosentan, and rezulin.

The present compositions can be administered together with treatment with irradiation or one or more chemotherapeutic agents. For irradiation treatment, the irradiation can be gamma rays or X-rays. For a general overview of radiation therapy, see Hellman, Chapter 12: Principles of Radiation Therapy Cancer, in: Principles and Practice of Oncology, DeVita et al., eds., $2^{nd}$. Ed., J.B. Lippencott Company, Philadelphia. Useful chemotherapeutic agents include methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel. In some embodiments, a composition of the invention further comprises one or more chemotherapeutic agents and/or is administered concurrently with radiation therapy. In some embodiments, chemotherapy or radiation therapy is administered prior or subsequent to administration of a present composition, such as at least an hour, five hours, 12 hours, a day, a week, a month, or several months (e.g., up to three months), subsequent to administration of a composition of the invention.

The present invention also provides compounds of the invention, or compositions comprising the same, for use in preventing pancreatic beta cell degeneration, treating a disorder associated with pancreatic beta cell degeneration, or treating or preventing type I diabetes in a mammal.

The present invention also provides compounds of the invention, or compositions comprising the same, for use in preparation of a medicament for preventing pancreatic beta cell degeneration, treating a disorder associated with pancreatic beta cell degeneration, or treating or preventing type I diabetes in a mammal.

EXAMPLES

Example 1

Oral Glucose Tolerance Test

Glucose was formulated in water at a concentration of 150 mg/ml and dosed at a volume of 10 ml/kg to produce a dose of 1.5 g/kg. Glucose was measured using the Ascensia II Elite XL glucose monitor (Sayer). Measure glucose by taking a small (2 mm) section off the tip of the tail, bleed onto glucose test strip and measure. Data for each time point analyzed by ANOVA and post-hoc Tukey's test. A p value of less then 0.05 was used to indicate statistical significance. Two studies were conducted with Compound 102.

In study 1, mice were dosed with Compound 102 and glucose as follows:

| Time (minutes) | Treatment/measure |
| --- | --- |
| 0 | Drug or vehicle |
| 15 | Glucose measure |
| 30 | Administer oral glucose |
| 45 | Glucose measure |
| 60 | Glucose measure |
| 90 | Glucose measure |
| 120 | Glucose measure |

In study 2, mice were dosed with Compound 102 and glucose as follows.

| Time (minutes) | Treatment/measure |
| --- | --- |
| 0 | Administer Drug |
| 15 | Glucose measure |
| 30 | Drug or vehicle |
| 30 | Administer oral glucose |
| 45 | Glucose measure |
| 60 | Drug or vehicle |
| 75 | Glucose measure |
| 90 | Drug or vehicle |
| 120 | Glucose measure |
| 150 | Glucose measure |

Study 3 tested Compound 102 and was conducted as follows:

| Time (minutes) | Treatment/measure |
| --- | --- |
| 0 | Drug or vehicle |
| 15 | Glucose measure |
| 30 | Administer oral glucose |
| 45 | Glucose measure |

| Time (minutes) | Treatment/measure |
| --- | --- |
| 60 | Glucose measure |
| 90 | Glucose measure |
| 120 | Glucose measure |

In study 1, a single administration of Compound 102 at a dose of 30 mg/kg significantly decreased normal blood glucose levels (pre-glucose loading) and significantly attenuated the blood glucose levels produced by oral glucose administration. Significance was lost 90 minutes after drug administration.

In study 2, with increased dosing, Compound 102 produced a more dramatic effect on blood glucose levels.

Compound 105 also produced dramatic reductions in blood glucose levels. A single dose of 2 or 10 mg/kg significantly ($p<0.05$) reduced blood glucose levels at all time points after administration. Baseline blood glucose levels were also significantly depressed (data not shown).

Example 2

Western Diet

Male CD1/ICR mice were obtained from Harlan. The study was started when mice were 8 weeks of age. Prior to initiation of the study mice fasted for 24 hrs. Mice were fed "Western Diet" that was designed to approximate the "typical" human diet of North America and Europe (Research Diets; New Brunswick, N.J.; Western Diet composition). The Western Diet contained greater then 5 times more fat then normal chow.

| Compound 102. Diet Compositions | | |
| --- | --- | --- |
| | Western Diet gm % | Normal Diet gm % |
| Protein | 20 | 16 |
| Carbohydrate | 50 | 61 |
| Fat | 21 | 4 |
| kcal/gm | 4.7 | 3.2 |

Mice were weighed daily beginning from the start of the 24 hr fasting period. Food intake was monitored continuously. Mice were bled by retroorbital eyebleed on days 7, 14, 21 and 28 after the initiation of the study. On day of REB mice were dosed 1× with full dose 1 hr prior to bleed. Fat pads were dissected at the end of the study (day 31) weighed and frozen. The following fat pads were dissected: brown, inguinal, axial, mesenteric, renal and epidydimal. Data were averaged and analyzed by ANOVA followed by a post-hoc Tukey's test with a p value of less then 0.05 indicating a statistical difference.

Administration of Compound 102 significantly reduced weight gain at the highest dose tested (30 mg/kg/day). This effect was apparent when measuring absolute weight and also when measuring weight change from day 0 (data not shown). Food intake was not affected by Compound 102 administration (data not shown).

Fat pads weights were significantly elevated in Western diet animals as compared to normal chow fed animals. Compound 102 administration significantly reduced brown, axial, inguinal, renal and epidydimal fat pad increases, but not mesenteric levels (data not shown).

Administration of Compound 102 produced a significant alteration in weight change in western diet fed animals that was independent of an effect on food intake and that was associated with reduction in fat pad development.

Example 3

Leptin Levels in Western Diet Treated Animals

Blood from mice that were on western diet (Compound 102) were analyzed for leptin levels. Mice were bled by retroorbital eyebleed on days 7, 14, 21 and 28 after the initiation of the study. On day of REB mice were dosed once with full dose 1 hr prior to bleed. Leptin levels were determined by ELISA (R&D Systems) as per directions. Data are expressed as the average±SEM. Data were averaged and analyzed by ANOVA followed by a post-hoc Tukey's test with a p value of less then 0.05 indicating a statistical difference.

Western diet led to a significant reduction in blood leptin levels as early as one week after initiation of the study. These leptin levels were not different from leptin levels of animals fed a normal diet. Administration of Compound 102 to animals fed a western diet reduced leptin levels to those fed a normal diet. This reduction may reflect a decrease in fat pad development and may be secondary to this event.

These data taken together with the data on weight gain, food intake and fat pad development indicate that animals fed a western diet and treated with Compound 102 do not look different from those fed a normal diet.

Example 4

In Vivo Db/Db Mouse Study

Db/Db and Db/lean mice were obtained from Harlan at 6 weeks of age. Mice were housed 3 per cage and fed ad libitum normal rodent chow. Mice were kept on a 12 hr Light:dark cycle.

The study was initiated when mice reached an age of 8 weeks and their baseline blood glucose levels were greater than 200 mg/dl. Compound 102 was formulated in PBS: 2N HCl (99:1) at concentrations of 0.5, 1.5 and 5 mg/ml. Mice were dosed at volumes of 10 ml/kg to produce doses of 5, 15 and 50 mg/kg/dose. Mice were dosed twice per day at an 8 hr interval (8 am and 4 pm) during the light cycle.

For the acute blood glucose measurements, blood glucose levels were measured after the animals received their first dose of Compound 102. Blood glucose levels were measured two hours after this initial injection.

Mice were administered vehicle or drug (i.e., Compound 102) (5, 15, and 50 mg/kg) twice per day (bid) for the 28 days. Mouse weight and food intake were monitored daily. Food intake is reported as food intake (grams) per mouse per 24 hr period.

In a Db/Db Leptin Receptor deficient diabetes/metabolic syndrome animal model, Compound 102 exhibited a dose dependent effect on both animal weight gain and blood glucose levels. In this study, mice were dosed with Compound 102 IP, twice/day over the course of four weeks. Significantly different animal weights were observed between Db/Db vehicle treated mice and mice receiving Compound 102 at doses of 5 mg/kg, 15mg/kg ($p<0.05$) and 50 mg/kg ($p<0.01$). Compound 102 has also been shown to reduce blood glucose levels following acute administration. Animals also demonstrated an acute dose response in the 15 mg/kg and 50 mg/kg dose groups upon study initiation and on weekly blood glucose testing.

When chronically administered to mice, Compound 102 significantly inhibited a weight-gain response to animals fed a high fat diet. There is no obvious trivial explanation for this effect. Most importantly, animals demonstrated normal food intake compared to vehicle-treated animals. Also, animals defecated normally and did not display the hyperactivity normally associated with the amphetamine class of weight-loss drugs.

Example 5

In Vivo Zucker Rat Study

Zucker rats and corresponding lean rats were supplied by Harlan. Rats were fed a normal diet, ad libitum, and kept on a 12 hr light/dark cycle. Rats were housed 3 per cage.

At 12 weeks of age, Zucker rats were administered Compound 102 at a concentration of 30 mg/kg (ip). Blood glucose levels were measured 30 minutes after administration. Forty-five minutes after drug administration, animals were administered a glucose solution (1.5 g/kg) by oral gavage. Blood glucose levels were measured every 30 minutes after gavage for 4.5 hrs.

There were 3 groups with 3 animals per group: 1) 3 Zucker leans (no drug; no glucose treatment); 2) Zucker vehicle treated group (glucose challenged) and 3) Zucker Compound 102 treatment (30 mg/kg); glucose challenged.

Oral glucose administration produced an elevation of blood glucose levels at two time points after administration: 30 and 270 minutes. Administration of Compound 102 reduced blood glucose levels at both time points.

Example 6

Figure 1B:
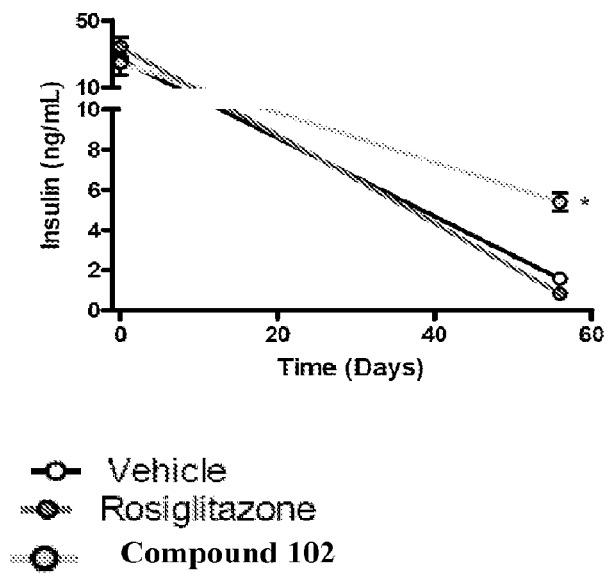

Decrease in Blood Glucose and Prevention of Loss of Serum Insulin Levels in db/db Mice Db/db mice were treated daily for 56 days with Compound 102 (30 mg/kg). Blood glucose levels were measured once per week and serum insulin levels measured at the beginning and at the end of the study. Administration of Compound 102 attenuated the progressive rise of blood glucose levels and significantly slowed the loss of serum insulin levels (see, FIGS. 1A and 1B).

Example 7

Prevention of Pancreatic β-Cell Degeneration in db/db Mice

Db/db mice were administered Compound 102 (100 mg/kg) for 60 days. At the end of the treatment period, pancreases were removed, post-fixed, sectioned and stained with insulin antibody to visualize pancreatic β-cells. Vehicle treated db/db mice expressed dramatically less insulin staining than lean control mice. Compound 102 treated mice expressed significantly higher levels of insulin staining than vehicle treated mice.

Figure 2:
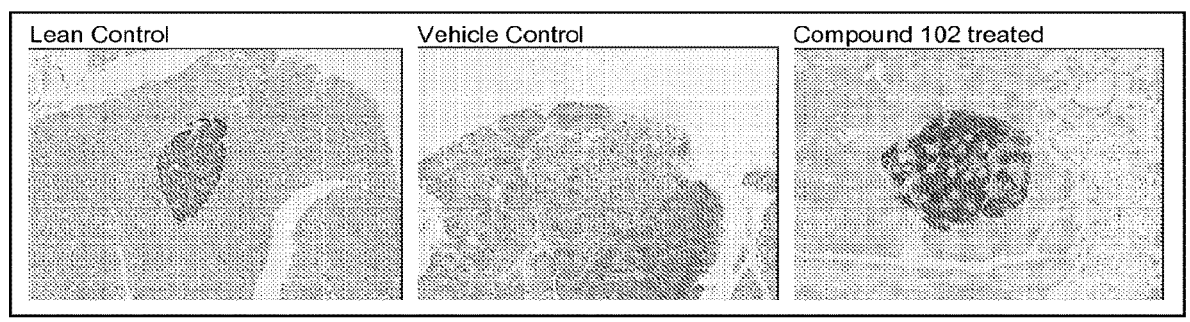
FIG. 2 illustrates the prevention of pancreatic β-cell degeneration in db/db mice upon administration of Compound 102.

Thus, db/db mice treated with Compound 102 do not exhibit the extent of serum insulin lowering associated with pancreatic β-cell loss as mice treated with vehicle or rosiglitazone. This apparent preservation of β-cell function was borne out in histological studies showing that islets from mice chronically treated with Compound 102 had increased insulin content and better preserved islet structure compared to untreated controls (see, FIG. 2). These data indicate that Compound 102 prevents β-cell degeneration in db/db mice.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims. A number of references have been cited, the entire disclosures of which are incorporated herein by reference.

What is claimed is:

1. A method of treating pancreatic beta cell degeneration by increasing insulin content and preserving islet structure in pancreatic islets in a human in need thereof comprising administering to the human in need thereof an effective amount of a composition comprising a compound of formula:

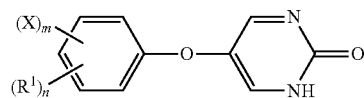

wherein:
$R^1$ is an alkyl group;
X is a halogen;
n is an integer from 0 to 5; and
m is 0 or 1;
wherein m+n is less than or equal to 5, thereby treating pancreatic beta cell degeneration.

2. The method of claim 1, wherein the alkyl group is methyl and n is 1.

3. The method of claim 1, wherein the halogen is chlorine and m is 1.

4. The method of claim 1, wherein $R^1$ is methyl, n is 1, and m is 0.

5. The method of claim 2, wherein $R^1$ is in the meta position.

6. The method of claim 1, wherein X is chlorine, n is 0, and m is 1.

7. The method of claim 6, wherein X is in the meta position.

8. A method of treating pancreatic beta cell degeneration by increasing insulin content and preserving islet structure in pancreatic islets in a human in need thereof comprising administering to the human in need thereof an effective amount of a composition comprising a compound of formula:

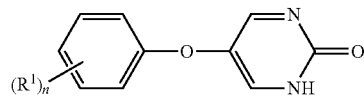

wherein $R^1$ is an alkyl group and n is an integer from 0 to 5, thereby treating pancreatic beta cell degeneration.

9. The method of claim 8, wherein $R^1$ is methyl, n is 1.

10. The method of claim 9, wherein $R^1$ is in the meta position.

11. A method of treating pancreatic beta cell degeneration by increasing insulin content and preserving islet structure in pancreatic islets in a human in need thereof comprising administering to the human in need thereof an effective amount of an oral composition comprising 0.5 mg to 20 mg per kg body weight of a compound of formula:

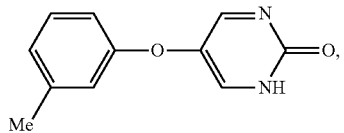 [SMILES: Cc1cccc(Oc2cnc(=O)[nH]c2)c1]

thereby treating pancreatic beta cell degeneration.

12. The method of claim 11, wherein the oral composition comprises 10% to 95% of the compound of the formula.

13. The method of claim 11, wherein the oral composition is a solution, suspension, emulsion, tablet, pill, capsule, or sustained-release formulation.

* * * * *